(12) United States Patent
Gosselin et al.

(10) Patent No.: US 12,310,976 B2
(45) Date of Patent: *May 27, 2025

(54) CORTICOSTEROID CONTAINING ORALLY DISINTEGRATING TABLET COMPOSITIONS FOR EOSINOPHILIC ESOPHAGITIS

(71) Applicant: Ellodi Pharmaceuticals, L.P., Lawrenceville, NJ (US)

(72) Inventors: Michael A. Gosselin, Springboro, OH (US); Jin-Wang Lai, Springboro, OH (US); Gopi M. Venkatesh, Vandalia, OH (US)

(73) Assignee: Ellodi Pharmaceuticals, L.P., Lawrenceville, NJ (US)

( * ) Notice: Subject to any disclaimer, the term of this patent is extended or adjusted under 35 U.S.C. 154(b) by 48 days.

This patent is subject to a terminal disclaimer.

(21) Appl. No.: 17/559,068

(22) Filed: Dec. 22, 2021

(65) Prior Publication Data

US 2022/0110945 A1 Apr. 14, 2022

Related U.S. Application Data

(60) Continuation of application No. 17/211,119, filed on Mar. 24, 2021, now Pat. No. 11,260,061, which is a continuation of application No. 16/578,568, filed on Sep. 23, 2019, now Pat. No. 11,166,961, which is a division of application No. 14/917,125, filed as application No. PCT/US2014/054203 on Sep. 5, 2014, now Pat. No. 10,471,071.

(60) Provisional application No. 61/874,450, filed on Sep. 6, 2013.

(51) Int. Cl.
| | | |
|---|---|---|
| A61K 31/56 | (2006.01) | |
| A61J 3/10 | (2006.01) | |
| A61K 9/00 | (2006.01) | |
| A61K 9/20 | (2006.01) | |
| A61K 45/06 | (2006.01) | |
| B29C 43/00 | (2006.01) | |

(52) U.S. Cl.
CPC ............ *A61K 31/56* (2013.01); *A61J 3/10* (2013.01); *A61K 9/0056* (2013.01); *A61K 9/2009* (2013.01); *A61K 9/2018* (2013.01); *A61K 9/2027* (2013.01); *A61K 9/2054* (2013.01); *A61K 9/2081* (2013.01); *A61K 9/2095* (2013.01); *A61K 45/06* (2013.01); *B29C 43/003* (2013.01); *B29C 43/006* (2013.01)

(58) Field of Classification Search
CPC .......................... A61K 9/0056; A61K 31/56
See application file for complete search history.

(56) References Cited

U.S. PATENT DOCUMENTS

| | | |
|---|---|---|
| 3,705,172 A | 12/1972 | Buchel et al. |
| 3,929,768 A | 12/1975 | Brattsand et al. |
| 4,080,448 A | 3/1978 | Mirsky |
| 4,335,121 A | 6/1982 | Phillipps et al. |
| 4,363,806 A | 12/1982 | Bergstrom et al. |
| 4,472,393 A | 9/1984 | Shapiro |
| 4,985,418 A | 1/1991 | Richards |
| 5,135,740 A | 8/1992 | Katz et al. |
| 5,252,337 A | 10/1993 | Powell |
| 5,278,175 A | 1/1994 | Ray et al. |
| 5,403,893 A | 4/1995 | Tanaka et al. |
| 5,446,070 A | 8/1995 | Mantelle |
| 5,482,934 A | 1/1996 | Calatayud et al. |
| 5,639,475 A | 6/1997 | Bettman et al. |
| 5,776,433 A | 7/1998 | Tzou et al. |
| 5,863,910 A | 1/1999 | Bolonick et al. |
| 6,139,865 A | 10/2000 | Friend et al. |
| 6,171,617 B1 | 1/2001 | Gruber |
| 6,316,027 B1 | 11/2001 | Johnson et al. |
| 6,495,160 B2 | 12/2002 | Esposito et al. |
| 6,534,549 B1 | 3/2003 | Newton et al. |
| 6,596,298 B2 | 7/2003 | Leung et al. |
| 6,596,311 B1 | 7/2003 | Dobetti |
| 6,740,332 B2 | 5/2004 | Zyck et al. |

(Continued)

FOREIGN PATENT DOCUMENTS

| | | |
|---|---|---|
| CA | 1027864 A | 3/1978 |
| CA | 2430481 A1 | 6/2002 |

(Continued)

OTHER PUBLICATIONS

Gentile et al., "Oesophageal narrowing is common and frequently under-appreciated at endoscopy in patients with oesophageal eosinophilia". Alimentary Pharmacology & Therapeutics (Dec. 2014); 40(11-12): 1333-1340. Epub Oct. 7, 2014.

German Patent Complaint Proceedings in the Regional Court, Mannheim, *Ellodi Pharmaceuticals, L.P.* vs. *Dr. Falk Pharma GmbH*, Docket No. 7 O 75/19, communication from the Regional Court of Mannheim giving Dr. Falk Pharma GmbH the opportunity to comment on the withdrawal of the complaint, dated Jul. 12, 2022, and Machine English translation, 2 pages.

(Continued)

*Primary Examiner* — Gina C Justice
(74) *Attorney, Agent, or Firm* — COOLEY LLP

(57) ABSTRACT

The present invention is directed to orally administered compositions of topically acting corticosteroids for the treatment of inflammation of the gastrointestinal tracts such as eosinophilic esophagitis. The present invention also provides a method for treating conditions associated with inflammation of the gastrointestinal tract in an individual. The method comprises administering to an individual in need thereof a pharmaceutical composition of the present invention as orally disintegrating tablets comprising a topically active corticosteroid adsorbed onto a pharmaceutically acceptable carrier such as silicified microcrystalline cellulose.

20 Claims, 1 Drawing Sheet

(56) References Cited

U.S. PATENT DOCUMENTS

| | | |
|---|---|---|
| 7,033,606 B1 | 4/2006 | Besse et al. |
| 7,122,198 B1 | 10/2006 | Singh et al. |
| 7,125,564 B2 | 10/2006 | Chen et al. |
| 7,229,641 B2 | 6/2007 | Cherukuri |
| 8,077,288 B2 | 12/2011 | Kawashima |
| 8,545,881 B2 | 10/2013 | Venkatesh et al. |
| 8,580,300 B2 | 11/2013 | Wilhelm et al. |
| 8,679,545 B2 | 3/2014 | Dohil et al. |
| 8,771,729 B2 | 7/2014 | Perrett et al. |
| 8,932,596 B2 | 1/2015 | Benhamou et al. |
| 9,387,167 B2 | 7/2016 | Perrett et al. |
| 9,486,407 B2 | 11/2016 | Perrett et al. |
| 9,782,347 B2 | 10/2017 | Dohil et al. |
| 9,849,084 B2 | 12/2017 | Perrett et al. |
| 9,867,780 B2 | 1/2018 | Greinwald et al. |
| 10,076,494 B2 | 9/2018 | Pevzner et al. |
| 10,105,315 B2 | 10/2018 | Meltzer et al. |
| 10,176,301 B2 | 1/2019 | Hill et al. |
| 10,272,037 B2 | 4/2019 | Dohil et al. |
| 10,471,071 B2 * | 11/2019 | Gosselin ............... B29C 43/006 |
| 10,632,069 B2 | 4/2020 | Perrett et al. |
| 10,869,592 B2 | 12/2020 | Ouyang et al. |
| 11,026,887 B2 | 6/2021 | Meltzer et al. |
| 11,166,961 B2 * | 11/2021 | Gosselin ............... A61P 29/00 |
| 11,246,828 B2 | 2/2022 | Perrett et al. |
| 11,260,061 B2 * | 3/2022 | Gosselin ............... A61J 3/10 |
| 11,266,598 B2 | 3/2022 | Perrett et al. |
| 11,684,571 B2 | 6/2023 | Meltzer et al. |
| 11,896,710 B2 | 2/2024 | Meltzer et al. |
| 12,059,494 B2 | 8/2024 | Meltzer et al. |
| 2001/0006625 A1 | 7/2001 | Bohn et al. |
| 2001/0014340 A1 | 8/2001 | Ohta et al. |
| 2003/0050312 A1 | 3/2003 | Hjorth et al. |
| 2003/0054036 A1 | 3/2003 | Liggins et al. |
| 2003/0099701 A1 | 5/2003 | Takaishi et al. |
| 2003/0215500 A1 | 11/2003 | Ohta et al. |
| 2004/0009212 A1 | 1/2004 | Tsai |
| 2004/0053902 A1 | 3/2004 | Smith |
| 2004/0106663 A1 | 6/2004 | Talley et al. |
| 2004/0228919 A1 | 11/2004 | Houghton et al. |
| 2004/0265375 A1 | 12/2004 | Platteeuw et al. |
| 2005/0009848 A1 | 1/2005 | Brantl |
| 2005/0112188 A1 | 5/2005 | Eliaz et al. |
| 2005/0232988 A1 | 10/2005 | Venkatesh et al. |
| 2006/0051414 A1 | 3/2006 | Ramalho et al. |
| 2006/0105038 A1 | 5/2006 | Lai et al. |
| 2006/0134054 A1 | 6/2006 | Kulkarni et al. |
| 2006/0292099 A1 | 12/2006 | Milburn et al. |
| 2007/0020330 A1 | 1/2007 | Dang et al. |
| 2007/0059361 A1 | 3/2007 | Rawas-Qalaji et al. |
| 2007/0111978 A1 | 5/2007 | Dohil et al. |
| 2009/0074862 A1 | 3/2009 | Schioppi et al. |
| 2009/0123390 A1 | 5/2009 | Hill |
| 2009/0123550 A1 | 5/2009 | Phillips et al. |
| 2009/0123551 A1 | 5/2009 | Phillips et al. |
| 2009/0131386 A1 | 5/2009 | Phillips |
| 2009/0149433 A1 | 6/2009 | Phillips |
| 2009/0155360 A1 | 6/2009 | Venkatesh et al. |
| 2009/0169620 A1 | 7/2009 | Venkatesh et al. |
| 2009/0181099 A1 | 7/2009 | Dohil et al. |
| 2009/0191275 A1 | 7/2009 | Dohil et al. |
| 2009/0264392 A1 | 10/2009 | Warndahl et al. |
| 2010/0034894 A1 | 2/2010 | Szymczak et al. |
| 2010/0215753 A1 | 8/2010 | Sherwood et al. |
| 2010/0216754 A1 | 8/2010 | Hill |
| 2011/0081411 A1 | 4/2011 | Perrett et al. |
| 2011/0097401 A1 | 4/2011 | Phillips et al. |
| 2011/0123460 A1 | 5/2011 | Wilhelm et al. |
| 2011/0129530 A1 | 6/2011 | Venkatesh et al. |
| 2012/0128764 A1 | 5/2012 | Venkatesh et al. |
| 2012/0164080 A1 | 6/2012 | Hill et al. |
| 2012/0282335 A1 | 11/2012 | Venkatesh et al. |
| 2013/0296286 A1 | 11/2013 | Dohil et al. |
| 2013/0310661 A1 | 11/2013 | Jedwab et al. |
| 2014/0187523 A1 | 7/2014 | Dohil et al. |
| 2014/0228714 A1 | 8/2014 | Chau et al. |
| 2014/0287051 A1 | 9/2014 | Perrett et al. |
| 2014/0303131 A1 | 10/2014 | Perrett et al. |
| 2014/0328861 A1 | 11/2014 | Payton et al. |
| 2015/0209432 A1 | 7/2015 | Konda et al. |
| 2015/0231156 A1 | 8/2015 | Phillips et al. |
| 2016/0045518 A1 | 2/2016 | Dohil et al. |
| 2016/0078186 A1 | 3/2016 | Hill et al. |
| 2016/0206627 A1 | 7/2016 | Gosselin et al. |
| 2016/0213681 A1 | 7/2016 | Santus et al. |
| 2016/0324772 A1 | 11/2016 | Greinwald et al. |
| 2017/0071855 A1 | 3/2017 | Perrett et al. |
| 2017/0183719 A1 | 6/2017 | Rothenberg et al. |
| 2018/0071211 A1 | 3/2018 | Dohil et al. |
| 2018/0133145 A1 | 5/2018 | Meltzer et al. |
| 2018/0153802 A1 | 6/2018 | Perrett et al. |
| 2019/0008760 A1 | 1/2019 | Meltzer et al. |
| 2019/0201333 A1 | 7/2019 | Dohil et al. |
| 2020/0016171 A1 | 1/2020 | Gosselin et al. |
| 2020/0214979 A1 | 7/2020 | Perrett et al. |
| 2020/0368147 A1 | 11/2020 | Meltzer et al. |
| 2020/0381097 A1 | 12/2020 | Meltzer |
| 2021/0205328 A1 | 7/2021 | Gosselin et al. |
| 2021/0244660 A1 | 8/2021 | Perrett et al. |
| 2021/0275438 A1 | 9/2021 | Meltzer et al. |
| 2021/0346278 A1 | 11/2021 | Meltzer et al. |
| 2022/0339098 A1 | 10/2022 | Perrett |
| 2022/0347189 A1 | 11/2022 | Nezamis et al. |
| 2023/0414498 A1 | 12/2023 | Meltzer et al. |
| 2024/0207288 A1 | 6/2024 | Eagle |

FOREIGN PATENT DOCUMENTS

| | | |
|---|---|---|
| CA | 2704946 A1 | 5/2009 |
| CA | 2776164 A1 | 4/2011 |
| CL | 38272008 | 12/2007 |
| CN | 1186428 A | 7/1998 |
| CN | 102665722 A | 9/2012 |
| CN | 105392497 A | 3/2016 |
| DE | 2323215 A1 | 11/1973 |
| DE | 4129535 A1 | 3/1992 |
| DE | 60202794 T2 | 5/2006 |
| DE | 202010018594 U1 | 2/2018 |
| EP | 0057401 A1 | 8/1982 |
| EP | 0440372 A1 | 8/1991 |
| EP | 1310243 A1 | 5/2003 |
| EP | 1323417 A1 | 7/2003 |
| EP | 1595533 A1 | 11/2005 |
| EP | 2886108 A1 | 6/2015 |
| EP | 2211896 B1 | 1/2018 |
| EP | 2482822 B1 | 8/2018 |
| EP | 2214679 B1 | 3/2019 |
| EP | 3041476 B1 | 11/2019 |
| EP | 3354276 B1 | 1/2020 |
| JP | S56138200 A | 10/1981 |
| JP | 11130679 A | 5/1999 |
| JP | H11511162 A | 9/1999 |
| JP | 2001524094 A | 11/2001 |
| JP | 2002521321 A | 7/2002 |
| JP | 2003509359 A | 3/2003 |
| JP | 2003261439 A | 9/2003 |
| JP | 2003292459 A | 10/2003 |
| JP | 2006077018 A | 3/2006 |
| JP | 2006516616 A | 7/2006 |
| JP | 2006516646 A | 7/2006 |
| JP | 2006524650 A | 11/2006 |
| JP | 2009519793 A | 5/2009 |
| JP | 2009521523 A | 6/2009 |
| JP | 2009173552 A | 8/2009 |
| JP | 2011503073 A | 1/2011 |
| JP | 2013506683 A | 2/2013 |
| KR | 20060123160 A | 12/2006 |
| KR | 10-2010-0087007 A | 8/2010 |
| KR | 20120104975 A | 9/2012 |
| KR | 20160058829 A | 5/2016 |
| RU | 2011134040 A | 2/2013 |
| RU | 2016104400 A | 8/2017 |
| WO | WO-9632095 A1 | 10/1996 |
| WO | WO-9706786 A1 | 2/1997 |

(56) References Cited

FOREIGN PATENT DOCUMENTS

| | | |
|---|---|---|
| WO | WO-9847535 A1 | 10/1998 |
| WO | WO-199947144 A1 | 9/1999 |
| WO | WO-0044351 A1 | 8/2000 |
| WO | WO-0064450 A1 | 11/2000 |
| WO | WO-0119342 A2 | 3/2001 |
| WO | WO-02092057 A1 | 11/2002 |
| WO | WO-03039520 A1 | 5/2003 |
| WO | WO-03093344 A1 | 11/2003 |
| WO | WO-2004064810 A1 | 8/2004 |
| WO | WO-2004067004 A1 | 8/2004 |
| WO | WO-2004069225 A1 | 8/2004 |
| WO | WO-2004091585 A1 | 10/2004 |
| WO | WO-2005087194 A1 | 9/2005 |
| WO | WO-2007071179 A1 | 6/2007 |
| WO | WO-2007074472 A2 | 7/2007 |
| WO | WO-2008098634 A1 | 8/2008 |
| WO | WO-2009064457 A2 | 5/2009 |
| WO | WO-2009064458 A2 | 5/2009 |
| WO | WO-2009064819 A2 | 5/2009 |
| WO | WO-2009086046 A1 | 7/2009 |
| WO | WO-2009098595 A2 | 8/2009 |
| WO | WO-2010021636 A1 | 2/2010 |
| WO | WO-2010144865 A2 | 12/2010 |
| WO | WO-2011041509 A1 | 4/2011 |
| WO | WO-2015006571 A1 | 1/2015 |
| WO | WO-2015034678 A2 | 3/2015 |
| WO | WO-2015035114 A1 | 3/2015 |
| WO | WO-2017189805 A1 | 11/2017 |
| WO | WO-2018035393 A1 | 2/2018 |
| WO | WO-2019165138 A1 | 8/2019 |
| WO | WO-2021067585 A1 | 4/2021 |
| WO | WO-2022020464 A1 | 1/2022 |
| WO | WO-2022225892 A1 | 10/2022 |
| ZA | 6805392 | 6/1969 |

OTHER PUBLICATIONS

German Utility Model Cancellation Proceedings DE 20201 018594 U1, *Dr. Falk Pharma GmbH* (Plaintiff/Respondent) vs. *Adare Pharmaceuticals US, L.P. / Ellodi Pharmaceuticals L.P.* (Patentee/Appellant), Notice of termination of proceedings dated Aug. 16, 2022, and English translation, 2 pages.
German Utility Model Cancellation Proceedings DE 20201 018594 U1, *Dr. Falk Pharma GmbH* (Plaintiff/Respondent) vs. *Adare Pharmaceuticals US, L.P. / Ellodi Pharmaceuticals L.P.* (Patentee/Appellant), Withdrawal of cancellation action dated Jul. 20, 2022, 1 page.
Opposition Proceedings in European Patent No. EP 2482822, Appeal No. T1954/21-3.3.01 (Appln. No. 10821232.5), filed by Dr. Falk Pharma GmbH on Mar. 1, 2019; EPO Communication dated Jul. 25, 2022 regarding Termination of opposition proceedings, 1 page.
Opposition Proceedings in European Patent No. EP 3086782 (Appln. No. 14814872.9), (in the name of Dr. Falk Pharma GmbH) filed by Ellodi Pharmaceuticals, L.P. on Jun. 26, 2019; Written decision on rejection of the opposition dated May 9, 2022, and English translation, 63 pages.
Opposition Proceedings in European Patent No. EP 3403654 (Appln. No. 18178891.0), filed by Dr. Falk Pharma GmbH; Decision to discontinue the opposition proceedings dated Sep. 5, 2022, 2 pages.
PCT/US2022/025297, International Search Report and Written Opinion mailed Jul. 29, 2022, 10 pages.
Takita et al., "Successful esophageal endoscopic submucosal dissection with a transoral endoscope after stepwise scope bougienage of post-endoscopic submucosal dissection stricture". JGH Open (Oct. 2, 20202); 5(1): 163-165. eCollection Jan. 2021.
U.S. Appl. No. 14/917,125, filed Sep. 5, 2014, US 2016-0206627, Jul. 21, 2016, U.S. Pat. No. 10,471,071, Nov. 12, 2019.
U.S. Appl. No. 16/578,568, filed Sep. 5, 2014, US 2020-0016171, Jan. 16, 2020, U.S. Pat. No. 11,166,961, Nov. 9, 2021.
U.S. Appl. No. 17/211,119, filed Mar. 24, 2021, US 2021-0205328, Jul. 8, 2021, U.S. Pat. No. 11,260,061, Mar. 1, 2022.
Sodikoff et al., "Therapeutic strategies in eosinophilic esophagitis: Induction, maintenance and refractory disease", Best Pract Res Clin Gastroenterol. (Oct. 2015); 29(5): 829-839.
Straumann et al., "Budesonide is effective in adolescent and adult patients with active eosinophilic esophagitis", Gastroenterology (Nov. 2010); 139(5): 1526-1537.
Straumann et al., "Long-term budesonide maintenance treatment is partially effective for patients with eosinophilic esophagitis", Clin Gastroenterol Hepatol. (May 2011); 9(5): 400-409.
Dellon E.S., "Safety and Efficacy of Budesonide Oral Suspension Maintenance Therapy in Patients With Eosinophilic Esophagitis", Clin Gastroenterol Hepatol. Mar. 2019; 17(4): 666-673.e8. Epub Jun. 12, 2018.
Extended European Search Report for European Application No. EP 20873169.5 dated Sep. 22, 2023, 9 pages.
Hirano, I., et al. "Randomised clinical trial: the safety and tolerability of fluticasone propionate orally disintegrating tablets versus placebo for eosinophilic oesophagitis", Aliment Pharmacol Ther. Apr. 2020;51(8):750-759. Epub Mar. 9, 2020.
Konikoff, et al., "A Randomized, Double-Blind, Placebo-Controlled Trial of Fluticasone Propionate for Pediatric Eosinophilic Esophagitis". Gastroenterology. Nov. 2006; 131(5): 1381-1391. Epub Aug. 16, 2006.
Schoepfer, et al., "Delay in diagnosis of eosinophilic esophagitis increases risk for stricture formation in a time-dependent manner". Gastroenterology. Dec. 2013; 145(6):1230-1236. Epub Aug. 13, 2013.
Straumann et al., "Budesonide Orodispersible Tablets Maintain Remission in a Randomized, Placebo-Controlled Trial of Patients With Eosinophilic Esophagitis". Gastroenterology. Nov. 2020; 159(5): 1672-1685. e5. Epub Jul. 25, 2020.
Aceves, et al., "Oral viscous budesonide: a potential new therapy for eosinophilic esophagitis in children". Am J Gastroenterol. (Oct. 2007); 102(10): 1-9. Epub Jun. 20, 2007.
Aceves, et al., "Topical viscous budesonide suspension for treatment of eosinophilic esophagitis". The Journal of Allergy and Clinical Immunology (Sep. 1, 2005); vol. 116, Issue 3, pp. 705-706. Epub Jul. 1, 2005.
Ahmed and Shah, "Formulation of low dose medicines—theory and practice." Am. Pharm. Rev (2000); 3(3): 9-14.
Ahmed, Monjur, "Eosinophilic esophagitis in adults: An update". World J Gastrointest Pharmacol Ther. (May 6, 2016); 7(2): 207-213.
Alexander, et al., "Review. Therapeutic Options for Eosinophilic Esophagitis". Gastroenterology & Hepatology (Jan. 1, 2011); 7(1): 59-61.
Auszug von European Pharmacopeia 6.0 (English language) 2.9.8; Jul. 23, 2007, 2 pages.
Auszug von European Pharmacopeia 8.0 (German language) 2.9.8; Jul. 15, 2013, 1 page.
Auszug von US Pharmacopeia 35 1217; May 1, 2012, 3 pages.
[Author Unknown] Definition of slow-release (downloaded from Merriam-Webster online athttps://www.merriam-webster.com/medical/slow-release); accessed Jul. 31, 2019, 1 page.
[Author Unknown] Definition of sustained-release (downloaded from Merriam-Webster online athttps://www.merriam-webster.com/dictionary/sustainedrelease#medicalDictionary); accessed Jul. 31, 2019, 1 page.
[Author unknown] DrugBank Accession Number, first approved 1990, DrugBank Accession No. DB00588, https://go.drugbank.com/drugs/DB00588, 14 pages.
[Author Unknown] Jorveza package leaflet (downloaded from the European Medicines Agency atwww.ema.europa.eu/en/medicines/human/EPAR/jorveza#product-informationsection); accessed Aug. 1, 2019, 8 pages.
[Author Unknown] Jorveza package leaflet, Jorveza 1mg orodispersible tablets, tablets package leaflet (PIL) for United Kingdom-Ireland, Mat-No. 1147370 (Losan Pharma), Dated Mar. 15, 2018, Date Code Falk: GB-IE/03.18, 2 pages.
[Author Unknown] Jorveza summary of product characteristics (downloaded from the European Medicines Agency atwww.ema.europa.eu/en/medicines/human/EPAR/jorveza#product-informationsection); first published Jan. 18, 2018, accessed Aug. 1, 2019, 9 pages.

(56) References Cited

OTHER PUBLICATIONS

[Author Unknown] Povidone (polyvinylpyrrolidone (PVP)) compound summary (downloaded from Wikipedia at https://en.wikipedia.org/wiki/Polyvinylpyrrolidone); accessed Jul. 31, 2019, 5 pages.

[Author Unknown] Solubility of budesonide (downloaded from https://pubchem.ncbi.nlm.nih.gov/compound/Budesonide#section=Solubility&fullscreen=true); information available as of Oct. 15, 2015, accessed Aug. 1, 2019, 1 page.

Author Unknown, WHT 3ME brochure Version 2.0; Fully Automated 4 in 1 Tablet Testing Instrument Pharma Test; publication date unknown.

Bauer, et al., "106 Chapter 5 Methods and Basic Operations". Lehrbuch der Pharmazeutischen Technologie (Textbook of pharmaceutical technology), With an introduction to biopharmacy (2006); (eds) Lippold, et al., 8th revised and updated edition, and English translation, 12 pages.

Beveridge, et al., "Novel Therapeutic Approaches to Eosinophilic Esophagitis". Gastroenterology & Hematology (Jun. 2020); 16(6): 294-301.

Bonnet, et al., "Formulation of a 3-months Stability Oral Viscous Budesonide Gel and Development of an Indicating Stability HPLC Method", Pharm Technol Hosp Pharm (2018); 3(2): 91-99.

Bower et al., "Manifestations and Treatment of Laryngeal Sarcoidosis". Am. Rev. Respir. Dis., 122(2): 325-332 (1980).

Breuer, et al., "Glossary of Terms Related to Pharmaceutics (IUPAC Recommendations 2009)" Pure Appl. Chem. (2009); 81 (5): 971-999.

Brunner, et al., "Gastrointestinal transit, release and plasma pharmacokinetics of a new oral budesonide formulation." British Journal of Clinical Pharmacology (2005); 61(1): 31-38.

Buckton, G., "Water sorption and near IR spectroscopy to study the differences between microcrystalline cellulose and silicified microcrystalline cellulose before and after wet granulation." International Journal of Pharmaceutics (Apr. 1999); 181 (1): 41-47.

Budesonid, https://www.chemie.de/lexikon/Budesonid.html, Jul. 12, 2019, and English version, Sep. 10, 2020, 3 pages.

Campieria et al., "Oral budesonide is as effective as oral prednisolone in active Crohn's disease," Gut, 41: 209-214 (1997).

Certified Priority Document U.S. Appl. No. 61/186,777, filed Jun. 12, 2009, 104 pages.

Daley-Yates, Peter T. "Inhaled corticosteroids: potency, dose equivalence and therapeutic index." British Journal of Clinical Pharmacology (2015); 80(3): 372-380.

Declaration of Stephen Perrett, MBA, Ph.D. dated Jul. 16, 2020, 6 pages.

Dellon, et al., "Efficacy of Budesonide vs Fluticasone for Initial Treatment of Eosinophilic Esophagitis in a Randomized Controlled Trial". Gastroenterology (2019); 157: 65-73.

Dilger, K., et al. "Active eosinophilic esophagitis is associated with impaired elimination of budesonide by cytochrome P450 3A enzymes." Digestion (2013); 87(2):110-117. Epub Jan. 25, 2013.

Dohil, et al., "Oral Viscous Budesonide Is Effective in Children With Eosinophilic Esophagitis in a Randomized, Placebo-Controlled Trial". Gastroenterol. (Aug. 2010); 139(2): 418-429.

Dolo-Dobendan®, 1.4 mg/10 mg lozenges package insert, Reference ID 3030657, Revised: Jan. 2015, with English translation, 7 pages.

Dr. Schleuniger, "Key factors influencing measured tablet hardness"; Pharmatron; 2011, 5 pages.

EPO Communication dated Apr. 25, 2019 in connection with Application No. EP 08848597.4, 13 pages.

Eurasian Application No. 201491358, Search Report (with English translation), issued Jan. 22, 2015, 4 pages.

European Application No. EP 19757814.9, Extended European Search Report dated Nov. 4, 2021, 11 pages.

European Application No. EP 10821232.5, Extended European Search Report dated Feb. 6, 2014, 10 pages.

European Application No. EP 14184844.0, Extended European Search Report dated Feb. 9, 2015, 7 pages.

European Application No. EP 14842811.3, Extended European Search Report dated Mar. 23, 2017, 6 pages.

European Application No. EP 17842162.4, Extended European Search Report dated Apr. 1, 2020, 8 pages.

European Application No. EP 18178891.0, Extended European Search Report dated Aug. 13, 2018, 3 pages.

European Application No. EP 19189185.2, Extended European Search Report dated Aug. 29, 2019, 9 pages.

European Application No. EP 19207287.4, Extended European Search Report dated Apr. 6, 2020, 9 pages.

Falcoz, et al., "Bioavailability of Orally Administered Micronised Fluticasone Propionate." Clinical Pharmacokinetics (2000); 39 Suppl. 1: 9-15.

Forum of the National Formulary of Japan, compilation, Drugs in Japan, 2009 edition, published 2008, p. 2161-2165 (and English translation/summary of pertinent paragraphs), 8 pages.

Furuta, et al., "Review article: the pathogenesis and management of eosinophilic oesophagitis". Alimentary Pharmacology & Therapeutics (2006); 24: 172-182.

Furuta, Glenn T., "Eosinophils in the Esophagus: Acid is Not the Only Cause". Journal of Pediatric Gastroenterology & Nutrition (Apr. 1998); 26(4): 468-471.

Furuta, Glenn T., et al. "Eosinophilic esophagitis in children and adults: a systematic review and consensus recommendations for diagnosis and treatment: sponsored by the American Gastroenterological Association (AGA) Institute and North American Society of Pediatric Gastroenterology, Hepatology, and Nutrition." Gastroenterology (2007); 133(4): 1342-1363.

Georgia Application No. AP 2010012674, Search Report (with English translation) dated Nov. 28, 2013, 11 pages.

German Patent Complaint Proceedings in the Regional Court, Mannheim, *Ellodi Pharmaceuticals, L.P. (formerly Adare Development I, L.P.)* vs.*Dr. Falk Pharma GmbH*, Docket No. 7 O 75/19, Defendant's Consent to Withdrawal filed Jul. 15, 2022, and English translation, 2 pages.

German Patent Complaint Proceedings in the Regional Court, Mannheim, *Ellodi Pharmaceuticals, L.P.* vs. *Dr. Falk Pharma GmbH*, Docket No. 7 O 75/19, Order concerning value under dispute dated Jul. 18, 2022, and English translation, 4 pages.

German Patent Complaint Proceedings in the Regional Court, Mannheim, *Ellodi Pharmaceuticals, L.P.* vs. *Dr. Falk Pharma GmbH*, Docket No. 7 O 75/19, Withdrawal Submission filed by Ellodi Pharmaceuticals, L.P., dated Jul. 11, 2022, and English translation, 2 pages.

German Patent Complaint Proceedings in the Regional Court, Mannheim, Germany, *Adare Development I, L.P.* vs. *Dr. Falk Pharma GmbH*, Docket No. 7 O 75/19, Official Order dated Feb. 12, 2020, and English translation, 5 pages.

German Patent Complaint Proceedings in the Regional Court, Mannheim, Germany, *Adare Development I, L.P.* vs. *Dr. Falk Pharma GmbH*, Docket No. 7 O 75/19, Official Order dated Feb. 13, 2020, and English translation, 3 pages.

German Patent Complaint Proceedings in the Regional Court, Mannheim, Germany, *Adare Development I, L.P.* vs. *Dr. Falk Pharma GmbH*, Docket No. 7 O 75/19, Pleadings as filed, dated Dec. 16, 2019, and English translation, 66 pages.

German Patent Complaint Proceedings in the Regional Court, Mannheim, Germany, *Adare Development I, L.P.* vs. *Dr. Falk Pharma GmbH*, Docket No. 7 O 75/19, Response to Rejoinder as filed, dated Feb. 6, 2020 (and English translation), 36 pages.

German Patent Complaint Proceedings in the Regional Court, Mannheim, Germany, *Adare Development I, L.P.* vs. *Dr. Falk Pharma GmbH*, Docket No. 7 O 75/19, Submission of Dr. Falk—rejoinder dated Jan. 30, 2020 (and English translation), 38 pages.

German Patent Complaint Proceedings in the Regional Court, Mannheim, Germany, *Adare Development I, L.P.* vs. *Dr. Falk Pharma GmbH*, Docket No. 7 O 75/19, Submission of Dr. Falk—statement of defense, filed Oct. 7, 2019 (and English translation), 14 pages.

German Patent Complaint Proceedings in the Regional Court, Mannheim, Germany, *Adare Development I, L.P.* vs. *Dr. Falk Pharma GmbH*, Docket No. 7 O 75/19, Submission of Dr. Falk dated Feb. 10, 2020, 6 pages, in German and English.

(56) References Cited

OTHER PUBLICATIONS

German Patent Complaint Proceedings in the Regional Court, Mannheim, Germany, *Adare Development I, L.P.* vs. *Dr. Falk Pharma GmbH,* Docket No. 7 O 75/19, Writ as filed, dated Feb. 11, 2020, and English translation, 5 pages.

German Patent Infringement Proceedings in the Regional Court, Mannheim, Germany, *Adare Development I, L.P.* vs. *Dr. Falk Pharma GmbH,* Docket No. 7 O 75/19, Patent Complaint dated Jul. 3, 2019, with English translation, 107 pages.

German Utility Model Cancellation Action filed by Dr. Falk Pharma GmbH on Mar. 1, 2019 with the German Patent Office, in connection with DE Patent No. 202010018594 U1 in the name of Adare Pharmaceuticals, Inc., and English translation, 21 pages.

German Utility Model Cancellation Proceedings DE 20201 018594 U1, *Dr. Falk Pharma GmbH* (Plaintiff/Respondent) vs. *Adare Pharmaceuticals US, L.P. / Ellodi Pharmaceuticals L.P.* (Patentee/Appellant), Statement of Grounds of Appeal dated Feb. 26, 2021 (and English translation), and Exhibit B817—Current EPA register extract on D5 dated Nov. 27, 2020, 117 pages.

German Utility Model Cancellation Proceedings, *Dr. Falk Pharma GmbH* (Plaintiff) vs. *Adare Development I, L.P.* (Patentee), Utility model DE 20201 018594 U1, Adare—Further Submission as filed dated Jul. 12, 2019, and English translation, 56 pages.

German Utility Model Cancellation Proceedings, *Dr. Falk Pharma GmbH* (Plaintiff) vs. *Adare Development I, L.P.* (Patentee), Utility model DE 20201 018594 U1, Auxiliary Request I-IV (marked-up) dated and as filed Jul. 1, 2020, and English translation, 17 pages.

German Utility Model Cancellation Proceedings, *Dr. Falk Pharma GmbH* (Plaintiff) vs. *Adare Development I, L.P.* (Patentee), Utility model DE 20201 018594 U1, Official Communication—Interlocutory Notice dated Jan. 22, 2020 (and English translation), 12 pages.

German Utility Model Cancellation Proceedings, *Dr. Falk Pharma GmbH* (Plaintiff) vs. *Adare Development I, L.P.* (Patentee), Utility model DE 20201 018594 U1, Response to Dr. Falk and Summons dated Jul. 2, 2020, and English translation, 18 pages.

German Utility Model Cancellation Proceedings, *Dr. Falk Pharma GmbH* (Plaintiff) vs. *Adare Development I, L.P.* (Patentee), Utility model DE 20201 018594 U1, Response to Pleadings as filed dated Oct. 17, 2019, and English translation, 25 pages.

German Utility Model Cancellation Proceedings, *Dr. Falk Pharma GmbH* (Plaintiff) vs. *Adare Development I, L.P.* (Patentee), Utility model DE 20201 018594 U1, Submission of Dr. Falk—Pleadings dated Sep. 13, 2019 (and English translation), 27 pages.

German Utility Model Cancellation Proceedings, *Dr. Falk Pharma GmbH* (Plaintiff) vs. *Adare Development I, L.P.* (Patentee), Utility model DE 202010018594 U1, Adare's Response dated Apr. 6, 2020 to Interlocutory Decision, and English translation, 29 pages.

German Utility Model Cancellation Proceedings, *Dr. Falk Pharma GmbH* (Plaintiff) vs. *Adare Development I, L.P.* (Patentee), Utility model DE 202010018594 U1, Communication from Adare to German Patent Office, Auxiliary Requests 1 and 2 (clean, marked-up and English translations) as filed Apr. 6, 2020, 23 pages.

German Utility Model Cancellation Proceedings, *Dr. Falk Pharma GmbH* (Plaintiff) vs. *Adare Development I, L.P.* (Patentee), Utility model DE 202010018594 U1, Submission of Dr. Falk—response to Adare and summons, dated Jul. 8, 2020 (and English translation), 11 pages.

German Utility Model Cancellation Proceedings, *Dr. Falk Pharma GmbH* (Plaintiff) vs. *Adare Development I, L.P.* (Patentee), Utility model DE 202010018594 U1, submission/Response by Dr. Falk Pharma GmbH dated Apr. 8, 2020 (and English translation), 18 pages.

Hahm and Augsburger, Orally Disintegrating Tablets and Related Tablet Formulations, Pharmaceutical Dosage Forms: Tablets, Third Edition, Ch. 9, vol. 2, Herausgeber: (eds) Larry L. Augsburger, Stephen W. Hoag, CRC Press (2008), 21 pages.

Ham, et al., "Quantitation of esophagal transit by means of 81mKr." European Journal of Nuclear Medicine (1984); 9: 362-365.

Handbook of Pharmaceutical Excipients (2009); Sixth Edition, ISBN 978 1 58212 135 2, (eds.) Rowe, et al., Cover Page, Print/Copyright and Preface Pages, 4 pages.

International Preliminary Report on Patentability for International Application No. PCT/US2017/047474, dated Feb. 19, 2019, 8 pages.

International Search Report and Written Opinion for International Application No. PCT/US2017/047474, mailed Dec. 26, 2017,11 pages.

Jorveza (budesonide) Update by the Committee for Medicinal Products for Human Use (CHMP), Summary of opinion1 (post authorisation) dated Mar. 26, 2020, European Medicines Agency, 1 page.

Katdare and Chaubal (eds)., Excipient Development for Pharmaceutical, Biotechnology and Drug Delivery Systems, Herausg. CRC Press, Taylor & Francis Group, Boca Raton, USA, 2006; dart: Excipients for Oral Liquid Formulations, S. 155-180, 28 pages.

Khan and Orenstein, "Eosinophilic Gastroenteritis: Epidemiology, Diagnosis and Management." Paediatr Drugs. (2002); 4(9): 563-570.

Krishna, et al., "Treatment of Eosinophilic Esophagitis Is Oral Viscous Budesonide Superior to Swallowed Fluticasone Spray?" Gastroenterol Hepatol (Jan. 2011); 7(1): 55-59.

Kumari and Rajendran, "Effect of topical nasal steroid spray in the treatment of non-specific recurrent/chronic pharyngitis-a trial study." Indian Journal of Otolaryngology and Head & Neck Surgery, 60(3): 199-201 (2008).

Langdon, BA and Mullamey, (2006) Handbook of Pharmaceutical Excipients. (eds.) Rowe, R.C., Sheskey, PJ and Owen, S.C., London: Pharmaceutical Press and American Pharmacists Association (extract—pp. 53-55 and 742-743), 14 pages.

Lee, Geoffrey, Professor, Report of Professor Geoffrey Lee, Ph.D. on measurement of disintegration time of "Jorveza 1 mg orodispersible tablet" dated Nov. 15, 2019, 16 pages.

Li, Xiaowei, et al., "Advances in Injectable Thermosensitive Polymers". Polymer Bulletin, No. 3, pp. 109-115, Jun. 30, 2015 (with English Abstract), 7 pages.

Liacouras, et al., "Primary Eosinophilic Esophagitis in Children: Successful Treatment with Oral Corticosteroids". Journal of Pediatric Gastroenterology & Nutrition (1998); 26(4): 380-385.

Lipka, et al., "The natural history of steroid-nave eosinophilic esophagitis in adults treated with endoscopic dilation and proton pump inhibitor therapy over a mean duration of nearly 14 years." Gastrointest Endosc. (2014); 80(4): 592-598.

Mahmoudi et al. "Effect of drug particle size on blend segregation and content uniformity". Contributed poster, AAPS Annual Meeting (USA) 2010, 1 page. (non-English).

Mahmoudi et al. "Influence of filler in blend uniformity of micronized drugs". Contributed poster, AAPS Annual Meeting (USA) 2010, 1 page.

Malaysian Application No. PI 2012001434, Search Report dated Jan. 29, 2016, 1 page.

Martin, et al., "Pediatric Eosinophilic Esophagitis Symptom Scores (PEESS® v2.0) identify histologic and molecular correlates of the key clinical features of disease". J Allergy Clin Immunol. (Jun. 2015); 135(6): 1519-1528.e8.

McGinity, J. W., et al. "Dissolution and uniformity properties of ordered mixes of micronized griseofulvin and a directly compressible excipient." Drug Development and Industrial Pharmacy, 11(4): 891-900 (1985).

Merck Index, "Budesonide," 14th Edition, p. 240 (2006).
Merck Index, "Ciclesonide," 14th Edition, p. 376 (2006).
Merck Index, "Clotrimazole," 14th Edition, p. 407 (2006).
Merck Index, "Mometasone Furoate," 14th Edition, pp. 1077-1078 (2006).
Merck Index, "Voriconazole," 14th Edition, p. 1728 (2006).

Miehlke, et al., "A randomised, double-blind trial comparing budesonide formulations and dosages for short-term treatment of eosinophilic oesophagitis", Gut (2016); 65: 390-399.

Moreton, R. Christian, "Disintegrants in Tableting". In book: Pharmaceutical Dosage Forms: Tablets, vol. 2, Herausgeber Augsburger & Hoag, CRC Press, Taylor and Francis Group (2008); Ch. 6, pp. 217-249, 33 pages.

(56) References Cited

OTHER PUBLICATIONS

New World Encyclopedia, "Gastrointestinal tract", https://web.archive.org/web/20090917122455/https://www.newworldencyclopedia.or . . . , Jul. 8, 2019, 7 pages.

New World Encyclopedia, "Gastrointestinal tract", https://www.newworldencyclopedia.org/entry/Gastrointestinal_tract, Jul. 8, 2019, 6 pages.

Nishimura, S., et al. "Factors associated with esophageal candidiasis and its endoscopic severity in the era of antiretroviral therapy." PLoS One (2013); 8(3): e58217, 6pgs.

Novopulmon E Novolizer, Instructions for the medical use of the medicament, [Instrukciya po medicinskomu primeneniyu preparata Novopulmon Novolizer (international nonproprietary name: budesonide), registracionniy nomer N LS-002405-231211, Dec. 21, 2011], MEDA Manufacturing, GmbH Registration No. LS-002405, Date of Registration Dec. 23, 2011 (with English summary of relevant portions), 9 pages.

"NUROFEN" tablet package insert, 200 MG Tablets and Capsules, Date of revision: Feb. 2018, Reference ID 3039860, and English version, 2 pages.

Opposition Proceedings in European Patent No. 2886108 (Appln. No. 13199278.6), filed by Adare Development, I, L.P on Nov. 6, 2019, EPO Communication dated Apr. 6, 2021, enclosing Patentee's Response to Submissions dated Mar. 30, 2021, and English translation, 9 pages.

Opposition Proceedings in European Patent No. EP 2482822 (Appln. No. 10821232.5), filed by Dr. Falk Pharma GmbH on Mar. 1, 2019; Appeal No. T1954/21-3.3.01 dated Jan. 4, 2022, 20 pages.

Opposition Proceedings in European Patent No. EP 2886108 (Appln. No. 13199278.6), filed by Ellodi Pharmaceuticals, L.P., on Nov. 6, 2019, Interlocutory Decision dated Jan. 5, 2022, and English translation, 43 pages.

Opposition Proceedings in European Patent No. EP 2886108 (Appln. No. 13199278.6), filed by Ellodi Pharmaceuticals, L.P., on Nov. 6, 2019, Minutes of Oral Proceedings dated Jan. 5, 2022, and English translation, 25 pages.

Opposition Proceedings in European Patent No. EP 3041476 (Appln. No. 14842811.3), filed by Dr. Falk Pharma GmbH on Jul. 22, 2020; EPO's Communication dated Nov. 18, 2021 enclosing Opponent's, Dr. Falk Pharma GmbH's Further Submissions dated Nov. 15, 2021, and English translation, 21 pages.

Opposition Proceedings in European Patent No. EP 3041476 (Appln. No. 14842811.3), filed by Dr. Falk Pharma GmbH on Jul. 22, 2020; Interlocutory Decision dated Feb. 14, 2022, 61 pages.

Opposition Proceedings in European Patent No. EP 3041476 (Appln. No. 14842811.3), filed by Dr. Falk Pharma GmbH on Jul. 22, 2020; Minutes of Oral Proceedings dated Feb. 14, 2022, and English translation, 15 pages.

Opposition Proceedings in European Patent No. 2482822 (Appln. No. 1082123205), filed by Dr. Falk Pharma GmbH on Mar. 1, 2019, D18—Dr F's novelty table 2020, 2 pages.

Opposition Proceedings in European Patent No. 2482822 (Appln. No. 1082123205), filed by Dr. Falk Pharma GmbH on Mar. 1, 2019, EPO Communication—communication of notice of opposition dated May 13, 2019, 1 page.

Opposition Proceedings in European Patent No. 2482822 (Appln. No. 1082123205), filed by Dr. Falk Pharma GmbH on Mar. 1, 2019, EPO Communication dated Nov. 5, 2019, enclosing Opponent's Further Written Submissions dated/filed on Oct. 29, 2019 (and English translation) including consolidated list of prior art, 29 pages.

Opposition Proceedings in European Patent No. 2482822 (Appln. No. 1082123205), filed by Dr. Falk Pharma GmbH on Mar. 1, 2019, EPO Communication dated Sep. 26, 2019, transmitting Adare's submission filed Sep. 20, 2019, 88 pages.

Opposition Proceedings in European Patent No. 2482822 (Appln. No. 1082123205), filed by Dr. Falk Pharma GmbH on Mar. 1, 2019, Notice of Opposition dated Mar. 1, 2019, and English translation, 23 pages.

Opposition Proceedings in European Patent No. 2482822 (Appln. No. 1082123205), filed by Dr. Falk Pharma GmbH on Mar. 1, 2019, Patentee, Adare Development I, L.P.'s Response dated Dec. 16, 2019 in response to further submissions filed by Dr. Falk Pharma GmbH on Oct. 29, 2019, 16 pages.

Opposition Proceedings in European Patent No. 2482822 (Appln. No. 1082123205), filed by Dr. Falk Pharma GmbH on Mar. 1, 2019, Submission filed by Adare Development I, L.P., on Sep. 20, 2019, 91 pages.

Opposition Proceedings in European Patent No. 2482822 (Appln. No. 10821232.5), filed by Dr. Falk Pharma GmbH on Mar. 1, 2019, EPO Communication dated Nov. 5, 2019, forwarding Letter from Opponent dated Oct. 29, 2019, 247 pages.

Opposition Proceedings in European Patent No. 2886108 (Appln. No. 13199278.6), filed by Adare Development, I, L.P on Nov. 6, 2019, Consolidated List of Cited Opposition Documents, 1 page.

Opposition Proceedings in European Patent No. 2886108 (Appln. No. 13199278.6), filed by Adare Development, I, L.P on Nov. 6, 2019, EPO Communication dated Jul. 24, 2020 regarding oral proceedings, 6 pages.

Opposition Proceedings in European Patent No. 2886108 (Appln. No. 13199278.6), filed by Adare Development, I, L.P on Nov. 6, 2019, EPO Communication dated Mar. 25, 2020 transmitting communication from Dr. Falk Pharma GmbH dated Mar. 20, 2020, and English translation, 34 pages.

Opposition Proceedings in European Patent No. 2886108 (Appln. No. 13199278.6), filed by Adare Development, I, L.P on Nov. 6, 2019, EPO Communication re Summons to Attend Oral Proceedings and Preliminary Opinion, dated Jul. 2, 2020, and English translation, 18 pages.

Opposition Proceedings in European Patent No. 2886108 (Appln. No. 13199278.6), filed by Ellodi Pharmaceuticals, L.P., on Nov. 6, 2019, Adare's Written Submissions in Preparation for Oral Proceedings on Apr. 23, 2021, dated Feb. 23, 2021, 25 pages.

Opposition Proceedings in European Patent No. 3086782 (Appln. No. 14814872.9), filed by Adare Development, I, L.P on Jun. 26, 2019, EPO Communication dated Jul. 2, 2019, transmitting Notice of Opposition filed Jun. 26, 2019, 43 pages.

Opposition Proceedings in European Patent No. 3086782 (Appln. No. 14814872.9), filed by Adare Development, I, L.P on Jun. 26, 2019, EPO Communication dated Jul. 22, 2020 regarding date of oral proceedings, 3 pages.

Opposition Proceedings in European Patent No. 3086782 (Appln. No. 14814872.9), filed by Adare Development, I, L.P on Jun. 26, 2019, EPO Communication dated Nov. 19, 2019, with Patentee's response to Opposition dated Nov. 8, 2019, and English translation, 22 pages.

Opposition Proceedings in European Patent No. 3086782 (Appln. No. 14814872.9), filed by Adare Development, I, L.P on Jun. 26, 2019, EPO Communication to Adare regarding oral proceedings dated Mar. 2, 2020, and English translation, 14 pages.

Opposition Proceedings in European Patent No. 3086782 (Appln. No. 14814872.9), filed by Adare Development, I, L.P on Jun. 26, 2019, Patentee, Dr. Falk's Written Submissions, Auxiliary Request I and Test Report Jorveza® 1 mg (dated Aug. 18, 2020, produced by Patentee, Dr. Falk Pharma), filed Sep. 10, 2020, and English translation, 22 pages.

Opposition Proceedings in European Patent No. EP 2482822, Appeal No. T1954/21-3.3.01 (Appln. No. 10821232.5), filed by Dr. Falk Pharma GmbH on Mar. 1, 2019; communication from the European Patent Office (EPO) dated May 18, 2022 enclosing Opponent's response to appeal dated May 12, 2022 and D27, and English translation, 44 pages.

Opposition Proceedings in European Patent No. EP 2482822, Appeal No. T1954/21-3.3.01 (Appln. No. 10821232.5), filed by Dr. Falk Pharma GmbH on Mar. 1, 2019; Ellodi's Withdrawal of Appeal dated Jul. 11, 2022, 3 pages.

Opposition Proceedings in European Patent No. EP 2482822, Appeal No. T1954/21-3.3.01 (Appln. No. 10821232.5), filed by Dr. Falk Pharma GmbH on Mar. 1, 2019; EPO's Communication—Minutes of Oral Proceeding, dated Aug. 25, 2021, and English translation, 11 pages.

(56) References Cited

OTHER PUBLICATIONS

Opposition Proceedings in European Patent No. EP 2482822 (Appln. No. 1082123205), filed by Dr. Falk Pharma GmbH on Mar. 1, 2019, Adare—Letter to EPO re Oral Proceedings dated Jul. 17, 2020, 5 pages.

Opposition Proceedings in European Patent No. EP 2482822 (Appln. No. 1082123205), filed by Dr. Falk Pharma GmbH on Mar. 1, 2019; Adare's Communication to the EPO re oral proceedings, dated Aug. 11, 2020, 4 pages.

Opposition Proceedings in European Patent No. EP 2482822 (Appln. No. 1082123205), filed by Dr. Falk Pharma GmbH on Mar. 1, 2019; EPO Communication dated Jul. 23, 2020, with Written Submission from Adare (Proprietor) dated Jul. 17, 2020, 126 pages.

Opposition Proceedings in European Patent No. EP 2482822 (Appln. No. 1082123205), filed by Dr. Falk Pharma GmbH on Mar. 1, 2019, EPO Communication dated Mar. 8, 2019 regarding notice of opposition, 1 page.

Opposition Proceedings in European Patent No. EP 2482822 (Appln. No. 1082123205), filed by Dr. Falk Pharma GmbH on Mar. 1, 2019; EPO's Communication re oral proceedings, dated Aug. 5, 2020, 1 page.

Opposition Proceedings in European Patent No. EP 2482822 (Appln. No. 1082123205), filed by Dr. Falk Pharma GmbH on Mar. 1, 2019, EPO Communication re Oral Proceedings dated Jul. 13, 2020, 3 pages.

Opposition Proceedings in European Patent No. EP 2482822 (Appln. No. 1082123205), filed by Dr. Falk Pharma GmbH on Mar. 1, 2019; EPO's consolidated list of cited opposition documents, Jul. 18, 2020, 1 page.

Opposition Proceedings in European Patent No. EP 2482822 (Appln. No. 1082123205), filed by Dr. Falk Pharma GmbH on Mar. 1, 2019, Summons to Attend Oral Hearing and Preliminary Opinion in opposition dated Feb. 13, 2020, 15 pages.

Opposition Proceedings in European Patent No. EP 2482822 (Appln. No. 1082123205), filed by Dr. Falk Pharma GmbH on Mar. 1, 2019, Summons to attend oral proceedings dated Feb. 13, 2020, 13 pages.

Opposition Proceedings in European Patent No. EP 2482822 (Appln. No. 1082123205), filed by Dr. Falk Pharma GmbH on Mar. 1, 2019; Written Submissions of the Patentee in Preparation for Oral Proceedings on Mar. 8, 2021, dated Jan. 8, 2021, with Auxiliary Requests 1-14, 52 pages.

Opposition Proceedings in European Patent No. EP 2482822 (Appln. No. 10821232.5), filed by Dr. Falk Pharm a GmbH on Mar. 1, 2019; EPO's Decision revoking European Patent No. 2482822, dated Aug. 25, 2021, 23 pages.

Opposition Proceedings in European Patent No. EP 2482822 (Appln. No. 10821232.5), filed by Dr. Falk Pharma GmbH on Mar. 1, 2019; EPO Communication in connection with Summons to attend oral proceedings, dated Nov. 20, 2020, 12 pages.

Opposition Proceedings in European Patent No. EP 2482822 (Appln. No. 10821232.5), filed by Dr. Falk Pharma GmbH on Mar. 1, 2019; Falk's Communication to the EPO re oral proceedings, dated Aug. 12, 2020, 3 pages.

Opposition Proceedings in European Patent No. EP 2482822 (Appln. No. 10821232.5), filed by Dr. Falk Pharma GmbH on Mar. 1, 2019, Opponent's response to Summons dated Jul. 17, 2020, and English translation, 15 pages.

Opposition Proceedings in European Patent No. EP 2482822 (Appln. No. 10821232.5), filed by Dr. Falk Pharma GmbH on Mar. 1, 2019; Written Submissions of the Opponent in response to the Summons to attend Oral Proceedings, dated and filed Dec. 8, 2020, and English translation, 37 pages.

Opposition Proceedings in European Patent No. EP 2886108, Appeal No. T0611/22-3.3.07 (Appln. No. 13199278.6), (in the name of Dr. Falk Pharma GmbH) filed by Ellodi Pharmaceuticals, L.P. on Nov. 6, 2019; EPO Communication dated May 27, 2022 confirming Termination of Appeal Proceedings filed May 16, 2022, 4 pages.

Opposition Proceedings in European Patent No. EP 2886108 (Appln. No. 13199278.6), filed by Adare Development I, L.P., on Nov. 6, 2019, Dr. Falk Pharma's Response to Summons and Adare's Written Submissions and clean and marked versions of Auxiliary Requests I and II, dated Dec. 18, 2020, and English translation, 26 pages.

Opposition Proceedings in European Patent No. EP 2886108 (Appln. No. 13199278.6), filed by Ellodi Pharmaceuticals, L.P., on Nov. 6, 2019, Datasheet for the decision of Oct. 14, 2019, Case Number T 1621/16-3.3.06, Application No. 09163237.2, 28 pages.

Opposition Proceedings in European Patent No. EP 2886108 (Appln. No. 13199278.6), filed by Ellodi Pharmaceuticals, L.P., on Nov. 6, 2019, Ellodi's Notice of Appeal against decision filed Mar. 4, 2022, 5 pages.

Opposition Proceedings in European Patent No. EP 2886108 (Appln. No. 13199278.6), filed by Ellodi Pharmaceuticals, L.P., on Nov. 6, 2019, Ellodi's Withdrawal of Appeal filed May 16, 2022, 3 pages.

Opposition Proceedings in European Patent No. EP 3041476, Appeal No. T1007/22-3.3.07 (Appln. No. 14842811.3), filed by Dr. Falk Pharma GmbH on Jul. 22, 2020; EPO Communication dated Jul. 22, 2022 confirming withdrawal of appeal as filed Jul. 14, 2022 by Opponent, 4 pages.

Opposition Proceedings in European Patent No. EP 3041476, Appeal No. T1007/22-3.3.07 (Appln. No. 14842811.3), filed by Dr. Falk Pharma GmbH on Jul. 22, 2020; EPO Communication dated Jun. 20, 2022 enclosing Opponent's Grounds of Appeal dated Jun. 10, 2022, and English translation, 27 pages.

Opposition Proceedings in European Patent No. EP 3041476, Appeal No. T1007/22-3.3.07 (Appln. No. 14842811.3), filed by Dr. Falk Pharma GmbH on Jul. 22, 2020; Withdrawal of Appeal filed by Ellodi Pharmaceuticals, L.P. dated Jun. 14, 2022, 3 pages.

Opposition Proceedings in European Patent No. EP 3041476 (Appln. No. 14842811.3), filed by Dr. Falk Pharma GmbH on Jul. 22, 2020; EPO Communication dated Feb. 22, 2021 enclosing Opponent's Submissions (and English translation), dated Feb. 16, 2021, 11 pages.

Opposition Proceedings in European Patent No. EP 3041476 (Appln. No. 14842811.3), filed by Dr. Falk Pharma GmbH on Jul. 22, 2020; EPO Communication dated Jul. 29, 2020 advising of and enclosing Notice of Opposition filed by Dr. Falk Pharma GmbH on Jul. 22, 2020, 82 pages.

Opposition Proceedings in European Patent No. EP 3041476 (Appln. No. 14842811.3), filed by Dr. Falk Pharma GmbH on Jul. 22, 2020; Notice of Appeal filed by Ellodi Pharmaceuticals, L.P. dated Apr. 22, 2022, 5 pages.

Opposition Proceedings in European Patent No. EP 3041476 (Appln. No. 14842811.3), filed by Dr. Falk Pharma GmbH on Jul. 22, 2020; Notice of Opposition and Statement of Grounds of Opposition (with English translation of Statement of Grounds of Opposition), and Consolidated List of references relied upon, filed Jul. 22, 2020, 513 pages.

Opposition Proceedings in European Patent No. EP 3041476 (Appln. No. 14842811.3), filed by Dr. Falk Pharma GmbH on Jul. 22, 2020; Patentee Adare's Response to Opposition dated .Jan. 11, 2021, 15 pages.

Opposition Proceedings in European Patent No. EP 3041476 (Appln. No. 14842811.3), filed by Dr. Falk Pharma GmbH on Jul. 22, 2020; Patentee Ellodi Pharmaceuticals, L.P.'s Written Submission in Preparation for Oral Proceedings on Dec. 8, 2021 with new Auxiliary Requests 1-3, dated Oct. 8, 2021, 51 pages.

Opposition Proceedings in European Patent No. EP 3403654 (Appln. No. 18178891.0), filed by Dr. Falk Pharma GmbH; Adare's Response to the Grounds of Opposition, filed Nov. 2, 2020, 78 pages.

Opposition Proceedings in European Patent No. EP 3403654 (Appln. No. 18178891.0), filed by Dr. Falk Pharma GmbH; Consolidated List of References dated and filed Dec. 8, 2020, 1 page.

Opposition Proceedings in European Patent No. EP 3403654 (Appln. No. 18178891.0), filed by Dr. Falk Pharma GmbH; EPO Communication of a notice of opposition dated Jun. 22, 2020, 1 page.

Opposition Proceedings in European Patent No. EP 3403654 (Appln. No. 18178891.0), filed by Dr. Falk Pharma GmbH; EPO Communication of a notice of opposition dated May 8, 2020, 1 page.

Opposition Proceedings in European Patent No. EP 3403654 (Appln. No. 18178891.0), filed by Dr. Falk Pharma GmbH; Opponent's Further Written Submissions dated and filed Dec. 8, 2020, and English translation, 30 pages.

(56) References Cited

OTHER PUBLICATIONS

Opposition Proceedings in European Patent No. EP 3403654 (Appln. No. 18178891.0), filed by Dr. Falk Pharma GmbH; Opponent's Submission/Withdrawal of Opposition dated Jul. 20, 2022, and English translation, 2 pages.
Opposition Proceedings in European Patent No. EP 3403654 (Appln. No. 18178891.0), filed by Dr. Falk Pharma GmbH; Statement of Grounds of Opposition filed on Apr. 28, 2020, and English translation, 38 pages.
Patent Complaint Proceedings in the Regional Court, Mannheim, Germany, *Adare Development I, L.P.* vs. *Dr. Falk Pharma GmbH,* Reference No. 4c O Oct. 2019, Decision (and English translation) dated Oct. 26, 2020, pronounced in the oral hearing of Jul. 21, 2020, 45 pages.
PCT Application No. PCT/US2010/050860, International Preliminary Report on Patentability dated Apr. 3, 2012.
PCT Application No. PCT/US2010/050860, International Search Report dated Feb. 10, 2011.
PCT Application No. PCT/US2010/050860, Written Opinion of the International Search Authority dated Feb. 10, 2011.
PCT Application No. PCT/US2014/052073, International Preliminary Report on Patentability dated Mar. 8, 2016.
PCT Application No. PCT/US2014/052073, International Search Report dated Nov. 20, 2014.
PCT Application No. PCT/US2014/052073, Written Opinion of the International Searching Authority dated Nov. 20, 2014.
PCT Application No. PCT/US2014/054203, International Preliminary Report on Patentability dated Mar. 8, 2016.
PCT Application No. PCT/US2014/054203, International Search Report dated Dec. 23, 2014.
PCT Application No. PCT/US2014/054203, Written Opinion of the International Searching Authority dated Dec. 23, 2014.
PCT Application No. PCT/US2019/019040, International Preliminary Report on Patentability, dated Aug. 27, 2020, 8 pages.
PCT Application No. PCT/US2019/019040, International Search Report and Written Opinion, mailed Jun. 25, 2019, 12 pages.
PCT Application No. PCT/US2019/019040, Invitation To Pay Additional Fees, mailed Apr. 25, 2019, 2 pages.
PCT/US2020/053778, International Preliminary Report on Patentability mailed Apr. 5, 2022, 7 pages.
PCT/US2020/053778, International Search Report and Written Opinion mailed Jan. 8, 2021, 9 pages.
PCT/US2021/042566, International Search Report and Written Opinion, mailed Nov. 5, 2021, 9 pages.
Pelle, et al., "Using defined daily doses to study the use of antibacterials in UK hospitals". Hosp Pharm (2006); 13: 133-136.
Ponchel, Gilles, "Formulation of oral mucosal drug delivery systems for the systemic delivery of bioactive materials". Advanced Drug Delivery Reviews, vol. 13, Issues 1-2, Jan.-Feb. 1994, pp. 75-87.
Ratnaparkhi, et al., "Review On: Fast Dissolving Tablet", Journal of Pharmacy Research. (Jan. 2009); 2(1): 5-12.
Remedios, et al., "Eosinophilic esophagitis in adults: clinical, endoscopic, histologic findings, and response to treatment with fluticasone propionate". Gastrointestinal Endoscopy (2006); 63(1): 3-12.
Robertson, et al., "Oesophageal transit of small tablets", J. Pharm. Pharmacol. (1988); 40: 595-596.
Schaefer, et al., "Comparison of Oral Prednisone and Topical Fluticasone in the Treatment of Eosinophilic Esophagitis: A Randomized Trial in Children". Clinical Gastroenterology and Hepatology (2008); 6: 165-173.
Schoepfer, et al., "Development and validation of a symptom-based activity index for adults with eosinophilic esophagitis". Gastroenterology (Dec. 1, 2014); 147(6): 1255-1266.
Singh, Arun, et al. "Oral candidiasis: An overview." Journal of Oral and Maxillofacial Pathology: JOMFP (2014); 18.Suppl 1: S81.
Sjostrom and Cairncross, "What Makes Flavor Leadership." Food Technology (1953); (7) 2: 56-58.

Supplementary European Search Report in European Patent Application No. EP 20192973.4, dated Nov. 18, 2020, 5 pages.
Taft, et al., "The adult eosinophilic oesophagitis quality of life questionnaire: a new measure of health-related quality of life". Alimentary Pharmacology & Therapeutics (Oct. 2011); 34(7): 790-798.
Taiwanese Application No. TW 099133628, Search Report (English translation) dated Nov. 16, 2014, 9 pages.
Taiwanese Application No. TW 104107443, Search Report (English translation) dated May 29, 2015,1 page.
Takaku, Fumimaro, et al. Manual of Therapeutic Agents 2007, Published 2007, p. 617-619 (and English translation/summary of pertinent paragraphs), 5 pages.
Tayebi and Mortazavi, "Formulation and Evaluation of a Novel Matrix-Type Orally Disintegrating Ibuprofen Tablet". Iran J Pharm Res. (2011 Summer); 10(3): 469-479.
Teitelbaum et al. "Eosinophilic esophagitis in children: immunopathological analysis and response to fluticasone propionate." Gastroenterology (2002), 122(5): 1216-1225.
Thorburn and Ferguson, "Topical corticosteroids and lesions of the oral mucosa". Advanced Drug Delivery Reviews, vol. 13, Issues 1-2, Jan.-Feb. 1994, pp. 135-149.
UM Complaint Proceedings in the Regional Court, Mannheim, Germany, *Adare Development I, L.P.* vs. *Dr. Falk Pharma GmbH,* Reference No. 4c O Oct. 2019, Replica dated Jul. 19, 2019, and English translation, 25 pages.
UM Complaint Proceedings in the Regional Court, Mannheim, Germany, *Adare Development I, L.P.* vs. *Dr. Falk Pharma GmbH,* Complaint dated Jul. 3, 2019, and English translation, 34 pages.
UM Complaint Proceedings in the Regional Court, Mannheim, Germany, *Adare Development I, L.P.* vs. *Dr. Falk Pharma GmbH,* Reference No. 4c O Oct. 2019, submission by Dr. Falk Pharma GmbH—statement of defense, dated May 24, 2019, and English translation, 16 pages.
UM Complaint Proceedings in the Regional Court, Mannheim, Germany, *Adare Development I, L.P.* vs. *Dr. Falk Pharma GmbH,* Reference No. 4c O Oct. 2019, Submission of Dr. Falk—Rejoinder dated Sep. 13, 2019 (English translation), 8 pages.
UM Complaint Proceedings in the Regional Court, Mannheim, Germany, *Ellodi Pharmaceuticals, L.P. (formerly Adare Development I, L.P.)* vs. *Dr. Falk Pharma GmbH,* Reference No. 4c O 10/2019, Defendant's Consent to Withdrawal filed Jul. 15, 2022, and English translation, 2 pages.
UM Complaint Proceedings in the Regional Court, Mannheim, Germany, *Ellodi Pharmaceuticals, L.P. (formerly Adare Development I, L.P.)* vs. *Dr. Falk Pharma GmbH,* Reference No. 4c O 10/2019, Order concerning value under dispute dated Jul. 20, 2022, and English translation, 2 pages.
UM Complaint Proceedings in the Regional Court, Mannheim, Germany, *Ellodi Pharmaceuticals, L.P. (formerly Adare Development I, L.P.)* vs. *Dr. Falk Pharma GmbH,* Reference No. 4c O 10/2019, Withdrawal Submission filed by Ellodi Pharmaceuticals, L.P., dated Jul. 11, 2022, and English translation, 2 pages.
Utility Model Cancellation Proceedings, *Dr. Falk Pharma GmbH* (Plaintiff) vs. *Adare Development I, L.P.* (Patentee), Utility model DE 202010018594 U1, Jul. 12, 2019—Exhibit BB1 "Breakdown of Features", and English translation, 2 pages.
Utility Model Cancellation Proceedings, *Dr. Falk Pharma GmbH* (Plaintiff) vs. *Adare Development I, L.P.* (Patentee), Utility model DE 202010018594 U1, Jul. 12, 2019—Exhibit BB4—Letter from Lederer & Keller dated Sep. 27, 2018 regarding European Patent No. 2211896, and Machine English translation, 28 pages.
Vogt et al., "Biowaiver monographs for immediate release solid oral dosage forms: Prednisolone," Journal of Pharmaceutical Sciences, 96(1): 27-37 (2007).
von Arnim and Malfertheiner, "Eosinophilic Esophagitis—Treatment of Eosinophilic Esophagitis with Drugs: Corticosteroids", Digestive Diseases (2014); 32: 126-129.
Webb, Paul A., "Surface Area, Porosity, and Related Physical Characteristics". In book: Pharmaceutical Dosage Forms: Tablets, 3rd Edition, vol. 3, CRC Press, Taylor and Francis Group, Boca Raton, London, New York (2008); Chapter 11, pp. 277-302.

(56) References Cited

OTHER PUBLICATIONS

Wechsler, Joshua B., et al. "Eosinophilic esophagitis reference score accurately identifies disease activity and treatment effects in children." Clinical Gastroenterology and Hepatology (2018); 16(7): 1056-1063.
Wei et al., "Efficacy of Single-Dose Dexamethasone as Adjuvant Therapy for Acute Pharyngitis" The Laryngoscope, 112(1):87-93 (2002).
Wikipedia, "Retard", https://de.wikipedia.org/wiki/Retard, Jun. 13, 2019, and Google machine translation, 7 pages.
Yalowsky and Bolton. "Particle size and content uniformity." Pharmaceutical Research, 7(9): 962-966 (1990).
Co-pending U.S. Appl. No. 18/287,416, inventor Eagle; Gina, filed on Oct. 18, 2023.
Faubion Jr., et al., "Treatment of eosinophilic esophagitis with inhaled corticosteroids". Journal of Pediatric Gastroenterology and Nutrition. Jul. 1, 1998; 27(1): 90-93, 6 pages.
International Preliminary Report on Patentability for International Application No. PCT/US2022/025297 dated Nov. 2, 2023, 8 pages.
Budenofalk®, Budenofalk®3mg, Dr. Falk Pharma GMBH, Brochure (6th Revised Edition 2005), 136 pages.
Budenofalk®, Budesonide Budenofalk®3mg, First-line-corticosteroid, Dr. Falk Pharma GMBH, Advertisement (2007), 1 page.
Curriculum Vitae of Alan F. Parr, Pharm.D., Ph.D., filed Jul. 22, 2024 in Petition for Inter Partes Review of U.S. Pat. No. 8,771,729 filed Jul. 22, 2024, 12 pages.
Danckwerts, M.D., "Intraoral Drug Delivery: A Comparative Review," American Journal of Drug Delivery (Sep. 2003); 1(3): 171-186.
Declaration of Alan F. Parr, Pharm.D., Ph.D., in Support of Petition for Inter Partes Review of U.S. Pat. No. 8,771,729 dated Apr. 17, 2024, filed Jul. 22, 2024, 174 pages.
Dr. Falk Pharma, "Where medicine and pharmaceuticals meet—a tried and trusted link", Dr. Falk Pharma GmbH, Brochure (2008), 29 pages.
"DRAFT Guidance: Guidance for Industry: Orally Disintegrating Tablets," U.S. Department of Health and Human Services, Food & Drug Administration, Center for Drug Evaluation and Research (CDER), Apr. 2007, 6 pages.
Elsing et al., "Budesonide for the treatment of obstructive eosinophilic jejunitis," Z. Gastroenterology Feb. 2007; 45(2): 187-189.
Fu et al., "Orally fast disintegrating tablets: developments, technologies, taste-masking and clinical studies," Critical Reviews in Therapeutic Drug Carrier Systems (2004); 21(6): 433-475.
Goodman & Gilman's: The Pharmacological Basis of Therapeutics, 11th edition, eds. Brunton, Lazo, Parker, 2006, Ch. 38, pp. 1014-1015, pp. 1246-1256, 15 pages.
"Guidance for Industry: Orally Disintegrating Tablets," U.S. Department of Health and Human Services, Food & Drug Administration, Center for Drug Evaluation and Research (CDER), Dec. 2008, 6 pages.
Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petition for Inter Partes Review of U.S. Pat. No. 8,771,729, dated and filed Jul. 22, 2024, including Exhibits and Petitioner Power of Attorney dated Mar. 24, 2024, 1079 pages.
Kolkman et al., "Evaluation of oral budesonide in the treatment of active distal ulcerative colitis," Drugs of Today Jul. 2004; 40(7): 589-601.
Noel et al., "Clinical and immunopathologic effects of swallowed fluticasone for eosinophilic esophagitis," Clinical Gastroenterology and Hepatology Jul. 2004; 2(7): 568-575.
Notice of Publication of FDA Guidance for Industry on Orally Disintegrating Tablets, Federal Register, vol. 73, No. 242 at 76366, Dec. 16, 2008, 1 page.
Opposition Proceedings in European Patent No. 2482822 B1 (Appln. No. 10821232.5), filed by Dr. Falk Pharma GmbH on Mar. 1, 2019, Adare Development I, L.P.'s (now Ellodi Pharmaceuticals, L.P.) Response to Grounds of Opposition dated Sep. 20, 2019, 27 pages.
Opposition Proceedings in European Patent No. EP 2482822 (Appln. No. 10821232.5), filed by Dr. Falk Pharma GmbH on Mar. 1, 2019; EPO's Decision revoking European Patent No. 2482822, dated Aug. 25, 2021, 31 pages.
Prosecution history excerpts from U.S. Appl. No. 12/896,005, filed Oct. 1, 2010, for Orally Administered Corticosteroid Compositions; Inventors Perrett, Stephen et al., issued as U.S. Pat. No. 8,771,729, 119 pages.
Prosecution history excerpts from U.S. Appl. No. 15/816,154 filed Nov. 17, 2017, for Orally Administered Corticosteroid Compositions; Inventors Perrett, Stephen et al., issued as U.S. Pat. No. 10,632,069, 90 pages.
Prosecution history excerpts from U.S. Appl. No. 17/236,295, filed Apr. 21, 2021, for Orally Administered Corticosteroid Compositions; Inventors Perrett, Stephen et al., issued as U.S. Pat. No. 11,266,598, 65 pages.
Shukla et al., "Mouth Dissolving Tablets I: An overview of formulation technology," Scientia Pharmaceutica (Mar. 6, 2009); 77(2): 309-326.
Siewert et al., "Eosinophilic gastroenteritis with severe protein-losing enteropathy: Successful treatment with budesonide," Digestive and Liver Disease Jan. 2006; 38(1): 55-59. Epub Dec. 1, 2005.
Svoboda et al., "Oral formulations of budesonide: a novel treatment for inflammatory bowel disease," Drugs of Today (Barc). Nov. 2008; 44(11): 857-863.
Tan et al., "Eosinophilic gastroenteritis treated with non-enteric-coated budesonide tablets," European Journal of Gastroenterology & Hepatology Apr. 2001; 13(4): 425-427.
The United States Pharmacopeia, "701 Disintegration", USP 32 (2009); NF 27, vol. 1, pp. 262-263, 4 pages.
Allen, L.V. and Luner, P.E., "Magnesium Stearate", Date of Revision: Aug. 9, 2005, In: Handbook of Pharmaceutical Excipients, 5th Ed. (2006), Raymond C. Rowe, et al. (eds); pp. 430-433, 7 pages.
Armstrong, N.A., "Mannitol", Date of Revision: Aug. 16, 2005, In: Handbook of Pharmaceutical Excipients, 5th Ed. (2006), Raymond C. Rowe, et al. (eds); pp. 449-453, 7 pages.
Conway, B.R., "Solid Dosage Forms", In: Pharmaceutical Manufacturing Handbook: Production and Processes (2008); by GAD, Shayne Cox; Ch. 4.1, pp. 235-265, 36 pages.
Declaration of Alan F. Parr, Pharm.D., Ph.D., in Support of Petition for Inter Partes Review (IPR2025-00052) of U.S. Pat. No. 10,632,069 dated Oct. 8, 2024, filed Oct. 24, 2024, 165 pages.
Declaration of Alan F. Parr, Pharm.D., Ph.D., in Support of Petition for Inter Partes Review (IPR2025-00054) of U.S. Pat. No. 11,246,828 dated Oct. 8, 2024, filed Oct. 24, 2024, 197 pages.
Declaration of Alan F. Parr, Pharm.D., Ph.D., in Support of Petition for Inter Partes Review (IPR2025-00055) of U.S. Pat. No. 9,486,407 dated Oct. 22, 2024, filed Oct. 24, 2024, 220 pages.
Declaration of Alan F. Parr, Pharm.D., Ph.D., in Support of Petition for Inter Partes Review (IPR2025-00056) of U.S. Pat. No. 11,260,061 dated Oct. 21, 2024, filed Oct. 24, 2024, 195 pages.
Definition of "Adsorption", McGraw-Hill Dictionary of Scientific and Technical Terms, Sixth Edition (2003); p. 41, 3 pages.
El-Arini, S.K., et al., "Evaluation of disintegration testing of different fast dissolving tablets using the texture analyzer", Pharm Dev Technol. 2002; 7(3): 361-371.
Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Preliminary Response, dated and filed Oct. 29, 2024, 59 pages.
Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Surreply, dated and filed Dec. 4, 2024, 8 pages.
Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petitioner's Reply to Patent Owner's Preliminary Response dated and filed Nov. 26, 2024, 8 pages.
Inter Partes Review Proceedings No. IPR2024-01197 filed Jul. 22, 2024, *Dr. Falk Pharma GMBH* (Petitioner) vs. *Ellodi Pharmaceu-*

(56) References Cited

OTHER PUBLICATIONS

*ticals LP* (Patent Owner), U.S. Pat. No. 8,771,729 (U.S. Appl. No. 12/896,005), Petitioner's Supplemental Mandatory Notice: Related Matters Section dated and filed Nov. 26, 2024, 4 pages.
Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 10,632,069 (U.S. Appl. No. 15/816,154), dated and filed Oct. 24, 2024, and Petitioner Power of Attorney dated Jun. 8, 2024, 83 pages.
Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 11,246,828 (U.S. Appl. No. 16/821,464), dated and filed Oct. 24, 2024, and Petitioner Power of Attorney dated Jun. 8, 2024, 91 pages.
Inter Partes Review Proceedings No. IPR2025-00055 filed Oct. 24, 2024, *Dr. Falk Pharma GMBH (Petitioner)* vs. *Ellodi Pharmaceuticals L.P.* (Patent Owner), Petition for Inter Partes Review of U.S. Pat. No. 9,486,407 (U.S. Appl. No. 14/294,660), dated and filed Oct. 24, 2024, and Petitioner Power of Attorney dated Jun. 8, 2024, 103 pages.
Inter Partes Review Proceedings No. IPR2025-00056 filed Oct. 24, 2024, *Dr. Falk Pharma GMBH (Petitioner)* vs. *Ellodi Pharmaceuticals L.P.* (Patent Owner), Petition for Inter Partes Review of U.S. Pat. No. 11,260,061 (U.S. Appl. No. 17/211,119), dated and filed Oct. 24, 2024, and Petitioner Power of Attorney dated Jun. 8, 2024, 107 pages.
Inter Partes Review Proceedings No. IPR2025-00056 filed Oct. 24, 2024, *Dr. Falk Pharma GMBH (Petitioner)* vs. *Ellodi Pharmaceuticals L.P.* (Patent Owner), Redline comparison of Dohil (US2007/0111978) and Dohil 2009 (US2009/0191275), Exhibit 1059 filed Oct. 24, 2024, 47 pages.
Khan et al., "An Approach for Rapid Disintegrating Tablet: a Review", IJPRD, May 2011; vol. 3(3): 21; pp. 170-183.
Kibbe, A.H., "Povidone", Date of Revision: Aug. 30, 2005, In: Handbook of Pharmaceutical Excipients, 5th Ed. (2006), Raymond C. Rowe, et al. (eds); pp. 611-616, 9 pages.
Martin, Alfred, et al., "Adsorption at Solid Interfaces", (with the participation of Pilar Bustamente), In: Physical Pharmacy: Physical Chemical Principles in the Pharmaceutical Sciences, Fourth Edition (1993); Print. No. 10, Ch. 14, pp. 379-386, 11 pages.
Moreton, R.C., "Cellulose, Silicified Microcrystalline", Date of Revision: Aug. 26, 2005, In: Handbook of Pharmaceutical Excipients, 5th Ed. (2006), Raymond C. Rowe, et al. (eds); pp. 139-141, 5 pages.
Opposition Proceedings in European Patent No. EP 3041476 (Appln. No. 14842811.3), filed by Dr. Falk Pharma GmbH on Jul. 22, 2020; Interlocutory Decision dated Jan. 26, 2022, 30 pages.
Price, J.C., "Polyethylene Glycol", Date of Revision: Aug. 29, 2005, In: Handbook of Pharmaceutical Excipients, 5th Ed. (2006), Raymond C. Rowe, et al. (eds); pp. 545-550, 8 pages.
Prosecution history excerpts from U.S. Appl. No. 14/917,125, filed Sep. 5, 2014, for Corticosteroid Containing Orally Disintegrating Tablet Compositions for Eosinophilic Esophagitis; Inventors Gosselin, Michael A., issued as U.S. Pat. No. 10,471,071, 123 pages.
Prosecution history excerpts from U.S. Appl. No. 17/211,119, filed Mar. 24, 2021, for Corticosteroid Containing Orally Disintegrating Tablet Compositions for Eosinophilic Esophagitis; Inventors Gosselin, Michael A., issued as U.S. Pat. No. 11,260,061, 248 pages.
Prosecution history from U.S. Appl. No. 15/816,154 filed Nov. 17, 2017, for Orally Administered Corticosteroid Compositions; Inventors Perrett, Stephen et al., issued as U.S. Pat. No. 10,632,069, 408 pages.
Prosecution history from U.S. Appl. No. 16/821,464, filed Mar. 17, 2020, for Orally Administered Corticosteroid Compositions; Inventors Perrett, Stephen et al., issued as U.S. Pat. No. 11,246,828, 369 pages.
Roeder et al., "Safety and Efficacy of Fluticasone Propionate in the Topical Treatment of Skin Diseases", Skin Pharmacol Physiol (2005); 18 (1): 3-11.
The United States Pharmacopeial Convention, "701 Disintegration", Revision Bulletin, Official Aug. 1, 2008, USP 32 (2009); 3 pages.
U.S. Appl. No. 18/244,500, inventor Meltzer, Brian A., et al., Brian, filed Sep. 11, 2023.
U.S. Appl. No. 18/755,113, inventor Meltzer; Brian A., filed Jun. 26, 2024.
Wen, Hong, (ed. Swarbick, James), "Adsorption at Solid Surfaces: Pharmaceutical Applications". Encyclopedia of Pharmaceutical Technology, Third Edition, vol. 1 (2007); pp. 34-38, 7 pages.
Wood, A.W., "Sucralose", Date of Revision: Aug. 17, 2005, In: Handbook of Pharmaceutical Excipients, 5th Ed. (2006), Raymond C. Rowe, et al. (eds); pp. 742-749, 11 pages.
Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Decision Granting Institution of Inter Partes Review 35 U.S.C. § 314 dated Jan. 27, 2025, 43 pages.
Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Supplemental Mandatory Notice: Related Matters Section dated and filed Dec. 17, 2024, 3 pages.
Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Petitioner's Supplemental Mandatory Notice: Related Matters Section dated and filed Dec. 17, 2024, 3 pages.
Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), Petitioner's Supplemental Mandatory Notice: Related Matters Section dated and filed Dec. 17, 2024, 3 pages.
Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Petitioner's Supplemental Mandatory Notice: Related Matters Section dated and filed Dec. 17, 2024, 3 pages.
Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Patent Owner's Objections Pursuant To 37 C.F.R. § 42.64(b)(1) dated Feb. 10, 2025, 12 pages.
Inter Partes Review Proceedings No. IPR2025-00056 filed Oct. 24, 2024, *Dr. Falk Pharma GMBH* (Petitioner) vs. *Ellodi Pharmaceuticals L.P.* , Declaration of Martyn Christopher Davies dated and filed Mar. 12, 2025, 62 pages.
Inter Partes Review Proceedings No. IPR2025-00056 filed Oct. 24, 2024, *Dr. Falk Pharma GMBH* (Petitioner) vs. *Ellodi Pharmaceuticals L.P.* , Patent Owner), Patent Owner's Response 37 C.F.R. § 42.107 dated and filed Mar. 12, 2025, 65 pages.

* cited by examiner

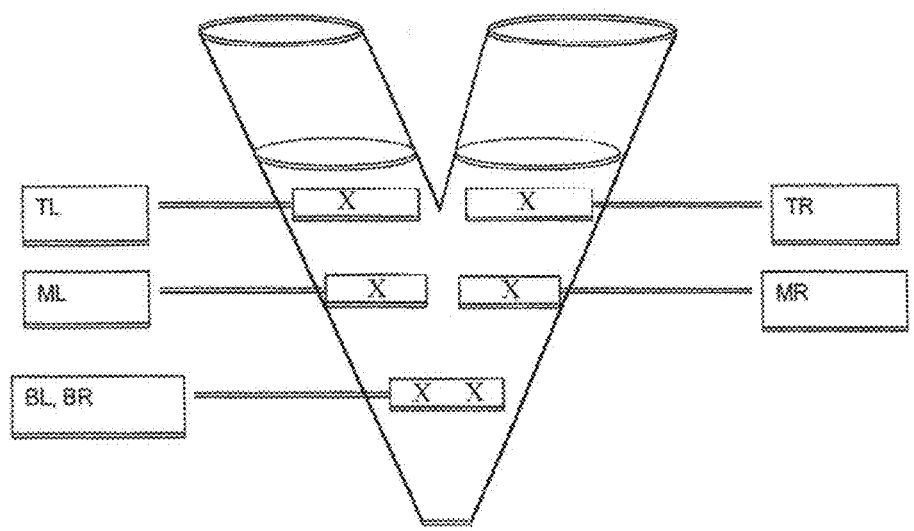

CORTICOSTEROID CONTAINING ORALLY DISINTEGRATING TABLET COMPOSITIONS FOR EOSINOPHILIC ESOPHAGITIS

CROSS-RELATED APPLICATIONS

This application is a Continuation of U.S. patent application Ser. No. 17/211,119, filed Mar. 24, 2021, which is a Continuation of U.S. patent application Ser. No. 16/578,568, filed Sep. 23, 2019 (U.S. Pat. No. 11,166,961, issued Nov. 9, 2021), which is a Divisional of U.S. patent application Ser. No. 14/917,125, filed Mar. 7, 2016 (U.S. Pat. No. 10,471,071, issued Nov. 12, 2019), which is the U.S. National Stage of International Patent Application No. PCT/US2014/054203, filed Sep. 5, 2014, which claims the benefit of priority under 35 USC § 119(e) of U.S. Provisional Patent Application No. 61/874,450, filed Sep. 6, 2013, disclosures of which are herein incorporated by reference in their entireties for all purposes.

FIELD OF THE INVENTION

This invention relates to orally administered low dose, topically acting corticosteroid compositions, useful for the treatment of conditions associated with inflammation of the esophagus.

BACKGROUND OF THE INVENTION

Esophageal inflammation disorders such as eosinophilic esophagitis (EoE) characterized by high levels of eosinophils in the esophagus, as well as basal zonal hyperplasia, are gaining increased recognition in children and adults. Many aspects of the disease remain unclear including its etiology, natural history, and optimal therapy. EoE affects all age groups but most frequently individuals between 20 and 50 years of age. Symptoms of EoE often mimic those of gastroesophageal reflux disease (GERD) and include vomiting, dysphagia, pain and food impaction. The common occurrence regarding misdiagnosis of EoE for GERD often results in delayed treatment in patients with EoE. There are currently no approved topically administered anti-inflammatory medications for the treatment of conditions associated with inflammation of the upper portion of the gastrointestinal tract, particularly the inflammatory conditions of the esophagus, i.e., EoE. The disease is painful, leads to difficulty swallowing and predisposes patients to food impaction and other complications. Although systemic treatments with corticosteroids such as prednisolone are effective, they are associated with significant adverse effects such as suppression of the hypothalamo-pituitary—adrenal (HPA) axis as reflected in salivary cortisol levels, generalized suppression of immune function, and particularly in children, troubling side-effects from long term systemic exposure include growth retardation, which may lead to a reduction in adult height.

In contrast, twice-daily treatments of EoE include directing steroid medications through a metered dose inhaler (MDI) to the back of the throat such that they are not appreciably inhaled, and instructing the patient to keep the mouth closed during the "puff and swallow" treatment and rinse the mouth immediately after administration, and not to swallow food or water for two hours after administration. Rinsing is recommended because residual drug in the mouth and throat can lead to candidiasis infection, and swallowing is contraindicated because it may wash drug away from the esophagus. In another study, 50% of fluticasone propionate (FP)-treated patients achieved histologic remission compared with 9% of patients receiving placebo (P=0.047), FP decreased esophageal eosinophil levels, with a more pronounced effect in non-allergic individuals. However, this therapy is particularly problematic for younger children and those with developmental delay, who are unlikely to utilize this puff and swallow technique effectively.

In another randomized, double blind, placebo controlled trial performed to evaluate the effect of oral 1 mg budesonide viscous solution (0.5 mg respule dissolved along with five 1-g packets of sucralose in 10-15 mL fluid) dosed twice daily vs. placebo in adolescent and adult patients with active EoE for 15 days, the pretreatment and post treatment disease activities were assessed clinically, endoscopically, and histologically. The primary end point was reduced mean numbers of eosinophils in the esophageal epithelium (number per high-power field [hpf]=esophageal eosinophil load). A 15-day course of treatment with budesonide is well tolerated and highly effective in inducing a histologic and clinical remission in adolescent and adult patients with active EoE. A 15-day course of therapy significantly decreased the number of eosinophils in the esophageal epithelium in patients given budesonide (from 68.2 to 5.5 eosinophils/hpf; P<0.0001); but not in the placebo group (from 62.3 to 56.5 eosinophils/hpf; P=0.48). Dysphagia scores significantly improved among patients given budesonide compared with those given placebo (5.61 vs 2.22; P<0.0001). White exudates and red furrows were reversed in patients given budesonide, based on endoscopy examination. This dosage form has not been FDA approved for commercial use, and the oral administration is going to be messy and likely to produce inconsistent results.

When oral solid dosage forms with a drug load of ≤5% by weight are required, the drug is either micronized and co-processed by blending with at least one carrier excipient or granulating in a fluid bed or high shear granulator by spraying preferably a solution of the drug to achieve blend uniformity/homogeneity of the blend and subsequently, content uniformity in the finished dosage units per regulatory requirements (FDA's Draft Guidance for Industry "Powder blend and finished dosage units—stratified in-process dosage unit sampling and assessment" October 2003). Many micronized drugs show a tendency to segregate and form larger particles in the blend in order to reduce their high surface energy, resultant segregation and agglomeration could cause resurfacing of the blend non-uniformity/inhomogeneity issues set out to resolve in the first place. Segregation and agglomeration in the blends containing especially poorly water soluble, low-dose drugs must be avoided not only during powder blending but also until processed into finished dosage forms, capsules or tablets, to achieve and maintain desired blend uniformity/homogeneity and/or to avoid high dissolution variability. Segregation of drug particles, especially in direct compression blends, is equipment and material dependent. It is thus very challenging to achieve acceptable blend homogeneity during direct compression blending of a low-dose drug with suitable pharmaceutically acceptable excipients (i.e., at a drug content of <5% by weight in the blend) and maintain the blend homogeneity until processing into finished dosage forms (e.g., tablets or capsules) (McGinity J. W. et al. Dissolution and uniformity properties of ordered mixes of micronized griseofulvin and a directly compressible excipient Drug Development and Industrial Pharmacy 1985; 11(4): 891-900; Yalkowsky S. H. and Bolton S. Particle size and content uniformity, Pharmaceutical Research, 1990; 7(9): 962-966; Ahmad H. and Shah N. Formulation of low dose medicines—Theory and Practice, *Amer. Pharm. Rev.* 2000; 3 (3): 1-5; Mahmoudi Z. N. et al. The influence of filler in blend uniformity of micronized drugs. Contributed poster, AAPS Annual Meeting (USA) 2010; Mahmoudi Z. N. et al. Effect of drug particle size on blend segregation and content uniformity. Contributed poster, AAPS Annual Meeting (USA) 2011).

WO2011041509 discloses the preparation of an orally administrable pharmaceutical composition containing a topically acting corticosteroid in an amount of less than 20 mg. Although there is no specific discussion of how to achieve acceptable blend uniformity in the working example of the compression blend which contains fluticasone propionate at only 4% by weight, which will be translated into achieving acceptable content uniformity of the ODTs, the fact that fluticasone is granulated with suitable pregranulated excipients, such as rapidly dispersing microgranules comprising mannitol and crospovidone, suggests that the granulation of fluticasone has been performed for the purpose of achieving acceptable content uniformity in the finished tablets. However, the micronized topically acting corticosteroid particles may be present in the agglomerated granules and as such may not be readily exposed to the inflamed EoE tissues upon oral administration for rapid induction of remission of EoE.

There is therefore a need for low-dose corticosteroid compositions having acceptable blend uniformity/homogeneity during blending of a topically acting corticosteroid with suitable pharmaceutically acceptable excipients as a carrier (i.e., at a drug content of <5%, especially at <3% by weight in the blend) and maintain the blend homogeneity until processing into finished unit dosage forms (e.g., tablets or capsules), which while exhibiting high content uniformity are suitable for oral administration in patients to provide topical (rather than systemic) treatment of inflammation of the of the upper gastrointestinal tract, particularly eosinophilic esophagitis (EoE) since the micronized, topically acting corticosteroid particles having been adsorbed largely on the surface of the carrier are capable of rapidly inducing remission of EoE.

SUMMARY OF THE INVENTION

The present invention is directed to an oral solid pharmaceutical composition comprising a low-dose topically acting corticosteroid and at least one pharmaceutically acceptable carrier for adsorption of the drug, wherein the drug is in an amount of less than about 5% (weight of drug/weight of composition), particularly less than 3% by weight and the composition has no significant systemic glucocorticoid or mineralocorticoid activity after oral administration in humans. The blend of a corticosteroid with the carrier has high blend uniformity/drug homogeneity which is translated into content uniformity of finished unit tablets.

The composition of the invention which can be formulated as an orally disintegrating tablet (hereafter referred to as an ODT) that disintegrates within 30 seconds when tested using the USP <701> Disintegration Test, and/or disintegrates within 60 seconds when placed in the oral cavity of a human.

The present invention is also directed to a process for making low dose pharmaceutical compositions comprising adsorbing a topically acting corticosteroid optionally micronized onto at least one pharmaceutically acceptable carrier such as silicified microcrystalline cellulose by blending for a sufficiently long time and passing through a de-segregating/comminuting mill at least once before blending with other pharmaceutically acceptable excipients, and then formulating the resulting blend into a suitable unit dose presentation, e.g., tableting.

The present invention discloses a method of preparing pharmaceutical compositions comprising especially poorly water soluble, low-dose, micronized drugs and at least one pharmaceutically acceptable carrier which must be blended for a sufficiently long time using a suitable blender-comminuting mill combination, thereby avoiding segregation-agglomeration of the drug particles in the blend not only during powder blending but also until processed into finished dosage forms, capsules or tablets, to achieve and maintain desired high blend uniformity/homogeneity and/or to achieve high content uniformity of the finished dosage units and also to avoid high dissolution variability.

The compositions of the present invention are useful for treatment of various conditions including the inflammatory conditions of the gastrointestinal tract. Accordingly, the present invention also provides a method for treating inflammatory conditions of the upper gastrointestinal tract in an individual particularly in the esophagus (eosinophilic esophagitis) via topical action with minimal systemic absorption and concomitant corticosteroid related side-effects. The method comprises administering to an individual to treat eosinophilic esophagitis a pharmaceutical composition of the present invention comprising topically acting optionally micronized corticosteroid particles adsorbed onto silicified microcrystalline cellulose. Alternatively, the compositions of the present invention may comprise a water soluble or water-swellable pharmaceutically acceptable excipient, such as bio-gelling or bioadhesive polymer that will enhance bioadherence of the corticosteroid to the inflamed esophageal mucosa.

DETAILED DESCRIPTION OF THE FIGURES

FIG. 1 shows the sampling locations in a blender for taking representative samples as per draft FDA Guidance (FDA's Draft Guidance for Industry "Powder blend and finished dosage units—stratified in-process dosage unit sampling and assessment" October 2003).

DETAILED DESCRIPTION OF THE INVENTION

The invention is directed to a solid pharmaceutical composition which comprises a corticosteroid in an amount of less than about 5% (weight of drug/weight of composition) and at least one pharmaceutically acceptable carrier for adsorption of the drug, wherein the composition has no significant systemic glucocorticoid or mineralocorticoid activity, and wherein the solid pharmaceutical composition disintegrates within 30 seconds when tested using the USP <701> disintegration method. The composition disintegrates in about 60 seconds or less on contact with saliva in the oral cavity of a subject or patient in need thereof.

The solid pharmaceutical composition of the present invention provides a therapeutically effective amount of a topical corticosteroid to inflamed tissues of the upper gastrointestinal tract, particularly to the esophageal inflamed tissues.

As used above, and throughout the description of the invention, the following terms, unless otherwise indicated, shall have the following meanings.

The term "drug", "active" or "active pharmaceutical ingredient" as used herein includes a pharmaceutically acceptable and topically acting corticosteroid, pharmaceutically acceptable salts, esters, solvates (including hydrates), polymorphs, stereoisomers, and/or prodrugs, and mixtures thereof. The terms "salts" refers to the product formed by the reaction of a suitable inorganic or organic acid with the "free base" form of the drug. Suitable acids include those having sufficient acidity to form a stable salt, for example acids with low toxicity such as the salt approved for use in humans or animals. Non-limiting examples of acids that may be used to form salts of a orally active drug, include inorganic acids, e.g., HCl, $H_3PO_4$ $H_2SO_4$. Non-limiting examples of organic acids include alkyl sulfonic acids and propionic acid.

The terms "orally disintegrating tablet", "orally dispersing tablet", or "ODT" refer to a solid dosage form of the present invention, which disintegrates rapidly in the oral cavity of a patient after administration, without chewing. The rate of oral disintegration can vary, but is significantly faster than the rate of oral disintegration of conventional solid dosage forms or chewable solid dosage forms (i.e., tablets or capsules) which are intended to be swallowed immediately after administration.

The term "about", as used herein to refer to a numerical quantity, includes "exactly". For example, "about 30 seconds" includes 30 seconds, exactly, as well as values close to 30 seconds (e.g., 25 seconds, 29 seconds, 31 seconds, 35 seconds, etc.). When the term "about" is used in reference to a range of values, the term "about" refers to both the minimum and maximum value of the range (e.g., "about 1-50 µm" means "about 1 µm to about 50 µm").

The term "intimately associated", as used herein to describe the spatial relationship between two or more components of a composition refers to components that are intimately mixed, such as, for example, in mixtures, coatings and matrices.

Unless indicated otherwise, all percentages and ratios are calculated by weight. Unless indicated otherwise, all percentages and ratios are calculated based on the total composition.

The term "having no significant systemic glucocorticoid or mineralocorticoid activity", as used herein refers to corticosteroid compositions which do not provide a generalized effect in the body through absorption into the circulation, but do provide local effects through topical contact with a diseased tissue. Corticosteroids which have high systemic glucocorticoid potencies when administered orally include e.g., hydrocortisone, prednisone, prednisolone, methylprednisolone, dexamethasone, betamethasone, etc. or mineralocorticoid potencies (e.g., alsosterone). Corticosteroids which typically have systemic glucocorticoid or mineralocorticoid activity when administered orally can also be used in the diluted compositions of the present invention, wherein the systemic uptake of the corticosteroid is reduced or suppressed.

Suitable topically acting corticosteroids which may be included in the pharmaceutical composition of the present invention include budesonide, fluticasone, flunisolide, ciclesonide, mometasone, beclomethasone, tixocortol and salts, or esters and mixtures thereof.

In a particular embodiment, the composition of the present invention comprises fluticasone. In other embodiments, the composition of the present invention comprises budesonide. In certain other embodiments, the composition of the present invention comprises ciclesonide.

In one embodiment, the corticosteroid may be in the form of crystals having a mean particle size of about 100 µm or less, about 75 µm or less, about 50 µm or less, more particularly about 25 µm or less, or about 15 µm or less. A particular embodiment of the invention is where the corticosteroid is micronized in order to achieve a mean particle size of less than about 10 µm, less than about 8 µm or less, less than about 6 µm, or particularly, less than about 4 µm. Alternatively, such crystals may have an average size in the sub-micron range (e.g., average particle size of about <1 µm), i.e., may be as nanoparticles (e.g., average particle size in the range of about 1-100 nm).

In another embodiment, the corticosteroid may be present in an amorphous form, for example in association with a stabilizing agent which limits drug recrystallization, e.g., polyvinylpyrrolidone (PVP), hydroxypropyl methylcellulose (HPMC), hydroxypropyl cellulose, hydroxyethycellulose; SOLUPLUS®, KOLLIDON® VA64, sodium lauryl sulphate, Tween surfactants, EUDRAGIT® EPO polymer, and mixtures thereof.

The amount of corticosteroid present in the pharmaceutical compositions of the present invention is selected so as to maximize the therapeutic benefit from topical administration while minimizing side effects from systemic absorption. In the case of solid pharmaceutical compositions of the present invention, the amount of corticosteroid in the composition is less than about 5% w/w (weight of drug/weight of composition). In one embodiment the amount of corticosteroid in the pharmaceutical composition is less than about 4%. In another embodiment it is less than about 3%. In yet another embodiment it is less than about 2%, less than about 1.5%, less than about 1%, less than about 0.5% by weight or less. In one embodiment the amount of corticosteroid in the pharmaceutical composition is between about 0.50 mg and about 18 mg. In still another embodiment the amount of corticosteroid in the pharmaceutical composition is between about 0.75 mg and about 12 mg. In yet another embodiment the amount of corticosteroid in the pharmaceutical composition is between about 1.5 mg and about 9 mg. In still other embodiments, the amount of corticosteroid is about 0.01 mg, about 0.05 mg, about 0.1 mg, about 0.15 mg, about 0.1 mg, about 0.2 mg, about 0.25 mg, about 0.3 mg, about 0.35 mg, about 0.4 mg, about 0.45 mg, about 0.5 mg, about 0.6 mg, about 0.7 mg, about 0.75 mg, about 0.8 mg, about 1 mg, about 1.5 mg, about 2 mg, about 3 mg, about 4 mg, about 4.5 mg, about 5 mg, about 6 mg, about 7 mg, about 8 mg, about 9 mg, about 10 mg, about 12 mg, about 18 mg, inclusive of all ranges and sub-ranges there between.

In the embodiment of the invention the rapidly disintegrating composition of the invention may comprise pharmaceutically acceptable excipients which swell, dissolve or otherwise facilitate disintegration of the ODT composition forming a smooth viscous suspension containing micronized corticosteroid particles to coat inflammatory esophageal mucosa to treat eosinophilic esophagitis. In certain embodiments of the present invention the total weight of the dosage form is kept in the range of from 300 to 900 mg to incorporate as much rapidly dispersing microgranules comprising at least one sugar alcohol in combination with at least one disintegrant, as possible to maximize eosinophilic esophagitis surface coating with micronized corticosteroid. In another embodiment, the rapidly dispersing microgranules comprise at least one disintegrant in combination with a sugar alcohol and/or a saccharide. The amount of sugar alcohol and/or saccharide in the rapidly dispersing granules ranges from about 99%-90%, or about 95%-90% of the total weight of the disintegrant-containing granules, including all ranges and sub-ranges there between. In one embodiment, the average particle size of a sugar alcohol and/or saccharide is about 30 µm or less, for example about 1-30 µm, about 5-30 µm, about 5-25 µm, about 5-20 µm, about 5-15 µm, about 5-10 µm, about 10-30 µm, about 10-25 µm, about 10-20 µm, about 10-15 µm, about 15-30 µm, about 15-25 µm, about 15-20 µm, about 20-30 µm, about 20-25 µm, or about 25-30 µm.

In one embodiment of the invention the dosage form has total weight of 300 mg and contain about 0.05 mg (0.16%), about 0.75 mg (0.25% w/w), about 1.5 mg (0.5% w/w), about 3 mg (1% w/w), about 4.5 mg (1.5%), about 6 mg (2% w/w), about 9 mg (3% w/w), about 12 mg (4% w/w), about 16 mg (5%) of the corticosteroid.

In another embodiment of the invention the dosage forms has total weight of 600 mg and contain about 0.75 mg (0.125% w/w), about 1.5 mg (0.25% w/w), about 3 mg (0.5% w/w), about 4.5 mg (0.75%), about 6 mg (0.1% w/w), about 9 mg (1.5% w/w), about 12 mg (2% w/w), about 18 mg (3% w/w) of the corticosteroid. In one embodiment of the invention the topically acting corticosteroid is fluticasone propionate and it is in the range of about 0.05 to about 15 mg in the pharmaceutical composition at a drug content of from about 0.16% to 5% by weight of the composition.

In another embodiment the fluticasone propionate is in the range of about 0.75 to about 4.5 mg in the composition at a drug content of from about 0.25% to 1.5% by weight in the composition.

In another embodiment the fluticasone propionate is in the range of 0.05 to about 18 mg in the composition at a drug content of from about 0.125% to 5% by weight in the composition.

The pharmaceutically acceptable carrier used in the mixture of the present invention is suitable for adsorption of the drug, it should have the properties of an excellent carrier for dry blends providing blend flowability and workability and preventing the segregation. It may concur in providing corticosteroid content uniformity. It is selected from the group consisting of microcrystalline cellulose, silicified microcrystalline cellulose, pregelatinized starch, corn starch, colloidal silica, or amorphous magnesium aluminum silicate (commercially available as VEEGUM™ or NEUSILIN™). It is preferably silicified microcrystalline cellulose which is composed of intimately associated microcrystalline cellulose and colloidal silicon dioxide particles, (PROSOLV® SMCC; MCC, 98% and CSD, 2%). The use of this ingredient in the composition of the invention improves the flow and blending properties of the corticosteroid mixture; improved blend uniformity/homogeneity and physical stability of the formulations during storage until their final processing into finished dosage forms such as tablets or capsules, i.e., to avoid or minimize potential de-mixing and segregation of corticosteroid microparticles is also achieved. The presence of this carrier in admixture with the active also ensures reproducibility of preparations of the composition of the invention (in particular with the applied technology of direct tableting). In one embodiment of the present invention a low dose corticosteroid blend with the carrier showing high blend uniformity, low segregation potential and excellent flowability is disclosed. This blend is particularly suitable for producing a rapidly disintegrating diluted corticosteroid composition. In one embodiment of the invention the blend comprises fluticasone propionate adsorbed on silicified microcrystalline cellulose, and rapidly dispersing microgranules.

The rate of disintegration of the compositions of the present invention in the oral cavity of an individual can be on the order of about 60 seconds or less, about 50 seconds or less, about 40 seconds or less, about 30 seconds or less, about 20 seconds or less, or about 10 seconds or less.

The rate of disintegration of the solid pharmaceutical compositions of the present invention measured using the USP <701> Disintegration Test is about 60 seconds or less, about 45 seconds or less, about 30 seconds or less, about 20 seconds or less, or about 10 seconds or less.

In addition to the corticosteroid and the carrier, the blend of the compositions or the oral dosage forms of the present invention may contain further pharmaceutically acceptable ingredients which swell, dissolve or otherwise facilitate disintegration. Such ingredients can include disintegrant, a sugar alcohol, a saccharide, or a mixture thereof, a water-soluble polymeric binder, a bio-gelling or a bioadhesive polymer, which can retain the corticosteroid particle adhered onto the inflamed esophageal tissues longer than in its absence.

In one embodiment, the present invention provides a solid pharmaceutical composition comprising a corticosteroid and a pharmaceutically acceptable bio-gelling polymer which enables longer retention of the corticosteroid at the inflamed esophageal tissues. The ingredient herein called "bio-gelling polymer" or "bio-adhesive agent" is an agent which promote adhesion of the corticosteroid to biological surfaces, especially the inflamed mucosa through gelling under GI tract physiological conditions, for example, upon contact with physiological fluids and/or at physiological temperature, and includes, but is not limited to the bin-gelling polymers listed below.

The bio-gelling polymer may be a thermosensitive polymer. Suitable thermosensitive polymers include polyacrylamides, such as poly(N-isopropylacrylamide), as well as poly(ether-ester) copolymers, such as poly(ethylene glycol-(DL-lactic acid-co-glycolic acid)-ethylene glycol). Such thermosensitive polymers can partially or fully cover the inflamed esophageal tissues while keeping the corticosteroid particle(s) close or in intimate contact with the inflamed tissues, thereby increasing the topical contact of the corticosteroid with the inflamed tissues.

In one embodiment, the composition of the present invention includes a bioadhesive agent such as a lipid or a polymer. Examples of such lipids are glycerphospholipids such as phosphatidyl choline, and diacyl glycerols such as glycerol dioleate. Examples of bioadhesive polymers include chitosan, polyorthoesters, and copolymers, terpolymers and mixtures thereof.

In another embodiment, the solid pharmaceutical compositions of the present invention include an adhesive agent. Suitable adhesive agents include sucrose aluminum sulfate complex, chitosan and derivatives such as trimethylchitosan, polyvinylpyrrolidone, methylcellulose, hydroxypropyl cellulose, cross-linked polyacrylic acid copolymers, polyvinylpyrrolidone, vinylpyrrolidone-polyvinyl acetate copolymer (e.g., KOLLIDON® VA 64 from BASF), SOLUPLUS®, poly(ethylene glycol 6000—vinylcaprolactam—vinyl acetate) (13:57:30) copolymer from BASF), polyvinyl alcohol, polyethylene oxide, polyamide, alginic acid and its salts, carrageenan, xanthan gum, ammoniomethacrylate copolymers, CARBOPOL polymers, maltodextrins, pectins, sucralose, and combinations thereof.

In certain embodiments of the solid pharmaceutical compositions of the present invention, the corticosteroid and the adhesive agent are intimately associated. In one such embodiment the solid pharmaceutical composition comprises corticosteroid surrounded or encapsulated by the adhesive agent. In another such embodiment the solid pharmaceutical composition comprises corticosteroid disposed on the surface of the adhesive agent. In still other embodiments, the solid pharmaceutical composition comprises corticosteroid mixed or granulated with the adhesive agent.

In certain embodiments of the present invention, the solid pharmaceutical composition includes any solid dosage form which disintegrates rapidly in the mouth to form a suspension of powdered corticosteroid, which is hypothesized to coat or adhere onto the inflamed esophageal mucosa when swallowed.

In one embodiment, the composition of the present invention is in the form of an ODT. The ODT comprises the drug is in amount less than about 5% (weight of drug/weight of composition) and a pharmaceutically acceptable carrier, wherein the composition has no significant systemic glucocorticoid or mineralocorticoid activity after oral administration in humans. The drug particles, (e.g., a corticosteroid as described herein optionally coated or optionally combined with an adhesive agent as described herein) are combined with rapidly dispersing microgranules. Rapidly dispersing microgranules comprise a sugar alcohol, a saccharide, or a mixture thereof and a disintegrant alone or a disintegrant in combination with a pharmaceutically acceptable additive with multi-functional activity (e.g., pregelatinized starch, hydroxypropylcellulose or the like).

A non-limiting list of suitable disintegrants for the rapidly dispersing microgranules includes crospovidone (cross-linked PVP), sodium starch glycolate, cross-linked sodium carboxymethylcellulose, calcium silicate, and low substituted hydroxypropyl cellulose.

The amount of disintegrant in the ODT is typically in the range of about 1% to about 10% by weight.

Sugar alcohols are hydrogenated forms of carbohydrates in which the carbonyl group (i.e., aldehyde or ketone) has been reduced to a primary or secondary hydroxyl group. Non-limiting examples of suitable sugar alcohols for the rapidly dispersing granules of the pharmaceutical compositions of the present invention include e.g., arabitol, isomalt, erythritol, glycerol lactitol, mannitol, sorbitol, xylitol, maltitol, and mixtures thereof. The term "saccharide" is synonymous with the term "sugars" includes monosaccharides such as glucose, fructose, the lactose, and ribose and disaccharides such as sucrose, lactose, maltose, trehalose, and cellobiose. In one embodiment, non-limiting examples of suitable saccharides for use in the compositions of the present invention include e.g., lactose, sucrose, maltose, and mixtures thereof. In another embodiment, the rapidly dispersing granules comprise at least one disintegrant in combination with a sugar alcohol. In another embodiment, the rapidly dispersing granules comprise at least one disintegrant in combination with a saccharide. In yet another embodiment, the disintegrant-containing granules comprise at least one disintegrant in combination with a sugar alcohol and a saccharide.

The amount of sugar alcohol and/or saccharide in the rapidly dispersing granules ranges from about 99%-90%, or about 95%-90% of the total weight of the disintegrant-containing granules, including all ranges and sub-ranges there between.

The amount of sugar alcohol and/or saccharide in the ODT ranges from about 30% to about 70% by weight.

In one embodiment, the average particle size of a sugar alcohol and/or saccharide is 30 μm or less, for example about 1-30 μm, about 5-30 μm, about 5-25 μm, about 5-20 μm, about 5-15 μm, about 5-10 μm, about 10-30 μm, about 10-25 μm, about 10-20 μm, about 10-15 μm, about 15-30 μm, about 15-25 μm, about 15-20 μm, about 20-30 μm, about 20-25 μm, or about 25-30 μm.

The ratio of the disintegrant to the sugar alcohol, saccharide, or mixture thereof in the rapidly dispersing microgranules ranges from about 90/10 to about 99/01, for example about 90/10, about 91/9, about 92/8, about 93/7, about 94/6, about 95/5, about 96/4, about 97/3, about 98/2, about 99/1, inclusive of all values, ranges, and sub-ranges there between.

The corticosteroid particles are typically adsorbed onto the carrier. The process for the preparation includes repeatedly mixing corticosteroid and carrier so that the blend is adsorbed onto the carrier. Corticosteroid is typically micronized (mean particle size of less than 10 μm) for the following reasons. Firstly, the finished dosage form (such as the ODT) is designed to rapidly disintegrate on contact with saliva in the oral cavity. In order to accomplish this, the dosage form (ODT) should have preferably a minimum of 100 mg of rapidly dispersing microgranules, irrespective of the dose of corticosteroid (for example, 0.1 mg, 1 mg, 10 mg or 20 mg). Secondly, in order to achieve blend uniformity/homogeneity in the blend and content uniformity of the finished unit dosage forms, a homogeneous distribution could be achieved by incorporating the micronized drug particles in silicified microcrystalline cellulose alone or in combination with rapidly dispersing microgranules by at least once blending and milling as described in examples of different embodiments of the present invention. The first option of incorporating the drug in the silicified microcrystalline cellulose will largely prevent segregation of corticosteroid microparticles during transient storage until final processing into finished dosage forms, capsules or tablets exhibiting high content uniformity and/or low dissolution variability.

Rapidly dispersing granules or granulate can be prepared as described in U.S. 2005/0232988 or U.S. 2003/0215500 by granulating a disintegrant with a sugar alcohol and/or saccharide having an average particle size of not more than about 30 μm. The granulation can be carried out, for example, in a high shear granulator with approximately 20-25% water as the granulating fluid, and if needed wet milled and dried to produce rapidly dispersing microgranules having an average particle size of not more than about 300 μm (e.g., about 175-300 μm). Rapidly dispersing microgranules can alternatively be prepared as described in U.S. Ser. No. 13/310,632 by granulating a sugar alcohol, a saccharide, or a mixture thereof and a disintegrant in combination with a pharmaceutically acceptable additive with multi-functional activity (e.g., starch, hydroxypropylcellulose or the like) at a low level of 0.5-3.0% by weight in a fluid bed granulator.

The rapidly dispersing microgranules present in the ODT help rapid disintegration of the tablet when placed in the oral cavity, creating a smooth suspension containing the corticosteroid drug particles. It is desirable to incorporate sufficient amount of rapidly dispersing microgranules to coat extensively the esophageal mucosa. This creates a content uniformity problem in these low-dose ODTs (for example, 300 mg ODT containing 12 mg or less of a corticosteroid). Typically, this problem is overcome by granulation, which involves spraying a dilute solution of the corticosteroid on to an excipient powder bed. The drug particles are embedded in the granules and consequently may not become exposed to the inflamed mucosa, resulting in being poorly efficacious. It has been surprisingly observed possible not only to achieve desired content uniformity but also enhance the probability of largely keeping the corticosteroid drug particles exposed to the inflamed mucosa by adsorbing micronized topically acting corticosteroid drug particles onto the pharmaceutically acceptable carrier (such as silicified microcrystalline cellulose) prior to blending with rapidly dispersing microgranules and other excipients and compressing into ODTs.

The dosage form as described herein may also include pharmaceutically acceptable excipients typically used in disintegrating tablet formulations such as fillers, diluents, glidants, disintegrants, binders and lubricants.

Examples of suitable fillers, diluents and/or binders include lactose (e.g. spray-dried lactose, such as FAST-FLO®), microcrystalline cellulose (various grades of AVICEL®, CEOLUS®), hydroxypropylcellulose, L-hydroxypropylcellulose (low substituted), low molecular weight hydroxypropyl methylcellulose (HPMC) (e.g., METHOCEL™ E, F and K from Dow Chemical, MetholoseE SH from Shin-Etsu, Ltd), hydroxyethylcellulose, sodium carboxymethylcellulose, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g., basic calcium phosphate, calcium hydrogen phosphate, dicalcium phosphate hydrate), calcium sulfate, calcium carbonate, sodium alginate and collagen. The preferred filler for the composition of the invention is mannitol such as spray dried mannitol.

Examples of suitable disintegrants include crospovidone (cross-linked PVP), sodium starch glycolate, cross-linked sodium carboxymethylcellulose, calcium silicate, and low substituted hydroxypropyl cellulose. The preferred disintegrant for the composition of the invention is cropovidone.

Specific examples of glidants and lubricants include stearic acid, magnesium stearate, calcium stearate or other metallic stearates, talc, glyceryl behenate, colloidal silica, corn starch, and optionally magnesium stearate or sodium stearyl fumarate (lubricant intragranularly mixed or used externally to lubricate die and punch surfaces). The preferred glidant for the composition of the invention is colloidal silica and preferred lubricant is sodium stearyl fumarate.

The solid pharmaceutical compositions of the present invention can include other dosage forms besides an ODT, a wafer, a film, or other solid dosage form which disintegrates rapidly in the mouth to form a suspension or dispersion of a corticosteroid, which can readily be swallowed to coat the mucosal surface of eosinophilic esophagitis.

For example, wafers can include dried or lyophilized compositions such as orally disintegrating or dissolving dosage forms prepared using ZYDIS® lyophilization technology (e.g., as described in U.S. Pat. No. 6,316,027), containing a corticosteroid as the active pharmaceutical ingredient. Film dosage forms can include edible films such as those described in U.S. Pat. Nos. 6,596,298 or 6,740,332, containing a corticosteroid as the active pharmaceutical ingredient. In one embodiment of the present invention the solid composition comprises a lyophilized matrix, wherein the lyophilized matrix comprises corticosteroid, the carrier and excipient. Suitable excipients include mannitol, xylitol, sorbitol, maltol, maltitol, lactose, sucrose, maltose, and combinations thereof.

Topical administration of a corticosteroid to the oral cavity of individuals has been associated with candidiasis infection. While the invention is designed so as be less prone to promoting such an infection, however in another embodiment of the invention, the pharmaceutical composition may include an antifungal agent. Suitable antifungal agents include, but are not limited to mitotic inhibitor antifungals, pyrimidine analog antifungals, polyene antifungals, benzimidazole antifungals, imidazole antifungals, polyene antifungals, triazole antifungals, thiazole antifungals, allylamine antifungals, echinocandin antifungals, and other "uncategorized" antifungals recognized in the art that do not fall within any of the above categories (e.g., tolnaflate and ciclopirox). For example, suitable antifungal agents which may be included in the solid pharmaceutical compositions of the present invention include abafungin, amorolfine, anidulafungin, bifonazole, butenafine, butoconazole, candicin, caspofungin, ciclopirox, clotrimazole, econazole, fenticonazole, filipin, fluconazole, flucytosine, griseofulvin, isavuconizole, isoconazole, itraconazole, ketoconazole, micafungin, miconazole, miconazole nitrate, naftifine, natamycin, nystatin, oxiconazole, posaconazole, pramiconazole, ravuconazole, rimocidin, setaconizole, sulconazole, terbafine, terconazole, tioconazole, tolnaftate, undecylenic acid, and voriconazole.

In another embodiment, pharmaceutical compositions of the present invention include an antiviral agent. Antiviral agents which may be included in the solid pharmaceutical compositions of the present invention include interferons, nucleoside and nucleotide reverse transcriptase inhibitors, non-nucleoside reverse transcriptase inhibitors, protease inhibitors, integrase inhibitors, fusion inhibitors, maturation inhibitors, guanosine analogs, puridine analogs, pyrimidine analogs, and other "uncategorized" antiviral drugs recognized in the art which do not fall within any of the above classes (e.g., foscarnet and miltefosine). For example, suitable antifungal agents which may be included in the solid pharmaceutical compositions of the present invention include abacavir, aciclovir (also known as acyclovir), adefovir, amantadine, amdoxovir, amprenavir, aplaviroc, apricitabine, arbidol, atazanavir, bevirimat, BMS-488043, boceprevir, brivudine, cidofovir, DCM205, docosanol, delavirdine, didanosine, durunavir, efavirenz, elvitegravir, elvucitabine, emtricitabine, enfuvirtide, epigallocatechin gallate, etravirine, famciclovir, fosamprenavir, ganciclocvir, globoidnan A, griffithsin, ibalizumab, idoxuridine, indinavir, lamivudine, lopinavir, loviride, maraviroc, nelfinavir, nevirapine, oseltamivir, pegylated interferon alpha-2a, pegylated interferon alpha-2b, penciclovir, peramivir, plerixafor, PRO 140, racivir, raltegrvir, ritonavir, ribavirin, rimantadine, rlipivirine, saquinavir, stampidine, stavudine, tenofovir, tipranavir, TNX-355, trifluridine, tromantadine, valaciclovir, valganciclovir, vicriviroc, vidarabione, viramidine, vivecon, zalcitabine, zanamivir, and zidovudine.

Tablet dosage forms, including ODT dosage forms, comprising the low dosage strength of a topically acting corticosteroid and a pharmaceutically acceptable carrier, wherein the drug is in amount less than about 5% (weight drug/weight of composition), have no significant systemic glucocorticoid or mineralocorticoid activity after oral administration in humans, disintegrate in less than about 30 sec (USP method), and have a low friability in order to have sufficient durability to withstand handling, shipping, and/or packaging in push-through blister packaging. Friability is less than about 1%, e.g., less than about 0.9%, less than about 0.8%, less than about 0.7%, less than about 0.6%, less than about 0.5%, less than about 0.4%, less than about 0.3%, etc., inclusive of all ranges and sub-ranges there between).

Different preparation processes can be applied to prepare blends of a corticosteroid with suitable carrier having blend homogeneity, i.e., acceptable blend uniformity and also content uniformity suitable for tableting. Blending the above ingredients can be achieved both by dry mixing or by granulation.

The present invention further discloses the method of manufacturing oral composition, such as compression or compressible blend at a drug load of from about 0.50 to about 3% by weight wherein it is challenging to achieve and maintain acceptable blend uniformity until the compression or compressible blend is processed into final unit dosage forms (e.g., orally disintegrating tablets) exhibiting acceptable content uniformity. The method comprises the following steps:

1) preparing the rapidly dispersing microgranules or granulate;
2) preparing the preblend 1 comprising charging a V-blender with one quarter of silicified microcrystalline cellulose (SMCC, a pharmaceutically acceptable carrier), micronized corticosteorid, colloidal silicon dioxide (a glidant) and another quarter of SMCC and blending the contents for 10 minutes;
3) preparing the preblend 2 comprising charging a high shear granulator with a free flowing filler (such as spray dried mannitol), preblend 1, remaining half of SMCC, disintegrant (such as crospovidone), and sweetener (sucralose powder) and blending the contents for 10 minutes at an impeller speed of 300±50 rpm and a chopper speed of 1500±50 rpm;
4) preparing the final compressible blend comprising charging a V-blender with one half of the rapidly dispersing granules of step 1, lubricant (such as sodium stearyl fumarate), the pre-blend 2 of step 3, and remaining half of rapidly dispersing granules of step 1 and blending for 30 minutes, sampled and further blended for 10±1 minutes to achieve acceptable blend uniformity/homogeneity as per regulatory requirements;
5) preparing the orally disintegrating tablets comprising the compressible blend of step 4, which exhibit acceptable content uniformity as per regulatory requirements.

In one embodiment, the method of manufacturing orally disintegrating tablets is performed by repeated dry blending and milling. The method comprises the following steps:

1) preparing the rapidly dispersing microgranules or granulate with an average particle size of not more than about 400 μm by granulating one or more sugar alcohols and/or saccharides, each having an average particle diameter of not more than about 30 μm, with a disintegrant (such as crospovidone) in presence of water or an alcohol-water mixture and then drying the granulate (fluid-bed equipment or a conventional oven);
2) preparing the milled preblend 1 by blending the pharmaceutically acceptable carrier (such as silicified microcrystalline cellulose), micronized corticosteroid and glidant (such as colloidal silicon dioxide) in a V-blender for 10 minutes at 25±1 rpm and then milling through a comminuting mill equipped with a 024R screen (30 Mesh opening) at approximately 2400±100 rpm;
3) preparing the milled preblend 2 by blending half of free flowing mannitol, preblend 1 from step 2, disintegrant (crospovidone), and sweetener (sucralose powder) in a V-blender for 10 minutes at 25±1 rpm and then milling through a comminuting mill equipped with a 024R screen at a speed of 2400±100 rpm, and rinsing the mill with remaining half of free flowing mannitol;
4) preparing the compressible blend by blending the rapidly dispersing granules of step 1, lubricant (such as sodium stearyl fumarate), the milled preblend 2 of step 3, rinsed free flowing mannitol) for total time of 40 minutes;
5) preparing the tablets by compressing the compressible blend of step 4.

The repeated dry blending and milling process is the preferred process for the preparation of the compositions of the invention.

In the process of the invention the different steps and the order of addition of individual components is important to achieve as acceptable blend uniformity/homogeneity in the compressible blend, as well as acceptable content uniformity of the finished dosage units as per regulatory requirements. The tablets obtained with the above process have the appearance, disintegration time, hardness and friability appropriate and suitable for ODTs to withstand attrition during transport in bulk containers, commercial packaging in blisters or bottles, and transport of primary/secondary packaged products for commercial distribution and end use and the purpose of the invention. Moreover, the tablets manufactured and then packaged in blisters are highly stable at accelerated and long-term ICH stability conditions.

The solid pharmaceutical compositions of the present invention are suitable for oral administration of a topically acting corticosteroid to treat inflamed tissues of the upper gastrointestinal tract, for example the esophagus. The use of a topically acting corticosteroid for treating conditions associated with inflammation of the gastrointestinal tract is desirable because it results in fewer side-effects than a highly systemically acting corticosteroid.

Inflammatory conditions of the gastrointestinal tract which may be treated according to the present invention include inflammation of the esophagus, inflammation of the glottis, inflammation of the epiglottis, inflammation of the tonsils, inflammation of the oropharynx, eosinophilic esophagitis, gastroesophageal reflux disease (GERD), non-erosive reflux disease (NERD), erosive esophagitis, Barrett's esophagus, eosinophilic gastroenteritis, hypereosinophilic syndrome, corrosive (caustic) chemical esophagitis, radiation-induced esophagitis, chemotherapy-induced esophagitis, transient drug-induced esophagitis (also known as medication esophagitis), persistent drug induced esophagitis, Crohn's disease of the esophagus, and pseudomembranous esophagitis.

In one specific embodiment, the pharmaceutical compositions of the present invention are suitable for treating inflammatory conditions of the upper gastrointestinal tract, particularly eosinophilic esophagitis.

Thus, the present invention includes pharmaceutical composition for use as medicaments in the treatment of inflammatory conditions of the gastrointestinal tract.

The invention also includes the method of administering to a patient in need thereof a solid pharmaceutical composition of the present invention. In one embodiment, the present invention includes a method for treating eosinophilic esophagitis comprising administering to a patient in need thereof a pharmaceutical composition of the present invention. Upon administration of a solid pharmaceutical composition of the present invention to an individual, the composition disintegrates in the patient's oral cavity. In another embodiment, the present invention includes a method for treating gastroesophageal reflux disease (GERD), nonerosive reflux disease (NERD) or erosive esophagitis comprising administering to an individual in need thereof a pharmaceutical composition of the present invention. In another embodiment, the present invention includes a method for treating a food allergy with an identified allergen, e.g., "atopic IBS", and "atopic bowel".

From the foregoing description and the experimental part, it can be seen that the present invention provides several important advantages. The described invention provides low dose oral compositions comprising a corticosteroid and a pharmaceutical carrier characterized by high content uniformity and stability, the composition and dosage forms wherein the corticosteroid microparticles are present largely at or near the surface of the carrier and are therefore likely to be suitably positioned for the topical treatment of inflammation of gastroenteric tract, particularly EoE, upon disintegration of the corticosteroid ODT in the oral cavity of a patient and swallowing of the resultant viscous suspension.

Experiments

Methods

Bulk/tapped density is measured according to USP <616> method 1.

Particle size distribution (PSD) is measured on samples of 5-10 mg with ATM sonic sifter.

Flowability is tested using Sotax flow tester on about 110 g of materials employing standard six pre-vibration/vibration mode; the flow property is expressed as a flow index ($\alpha'/\alpha_{ref}$) and as Carr's index.

Water content is determined using Karl Fisher titration or LOD is measured according to USP<921> 1a method.

Blend Uniformity Testing: Blend uniformity testing is carried out by withdrawing 6 random samples using a sampling thief from different locations of the final direct compression blend contained in the V- or twin shell blender as shown in FIG. 1. Samples collected are tested for their drug contents using an HPLC stability-indicating method.

Content Uniformity of ODTs: Orally disintegrating tablets are randomly sampled at the beginning, middle and end of each compression run, 10 tablets are tested for their content uniformity using the HPLC stability-indicating method.

Disintegration is performed according to USP<701> method. Friability is measured according to USP<1216> method.

EXAMPLES

Example 1

Rapidly Dispersing Microgranules

Rapidly dispersing microgranules are prepared following the procedure disclosed in US Patent Application Publication No. U.S. 2003/0215500 published Nov. 20, 2003, the contents of which are hereby incorporated by reference in its entirety for all purposes. Specifically, D-mannitol (152 kg) with an average particle size of approximately 20 µm or less (PEARLITOL® 25 from Roquette, France) is blended with 8 kg of cross-linked povidone (CROSPOVIDONE® XL-10 from ISP) in a high shear granulator (GMX 600 from Vector), granulated with purified water (approximately 32 kg), wet-milled using a Comil from Quadro, and finally tray-dried to provide microgranules having an LOD (loss on drying) of less than about 1.0%. Alternatively, the wet milled granules are dried in a fluid-bed dryer to provide microgranules having an LOD of less than 1.0% by weight. The dried granules are sieved and oversize material is again milled to produce rapidly dispersing microgranules with an average particle size in the range of approximately 175-300 microns.

D-mannitol with a median particle size of <20 µm (93 parts) and Crospovidone (5 parts) are granulated by spraying the starch solution (2 parts of STARCH 1500® from Colorcon) in a top spray fluid-bed granulator and dried for a loss on drying of <1.0%. The dried granules are sieved through a 20 mesh sieve, and oversized granules are milled and sieved, if needed to produce alternate rapidly dispersing granules.

Example 2

Blend Preparation by High Shear Process for 1.5 mg Fluticasone ODT; Batch 1

A preblend 1 is first prepared by blending one quarter of silicified microcrystalline cellulose (SMCC commercially available as PROSOLV® HD90), micronized fluticasone propionate, colloidal silicon dioxide, and another quarter of SMCC in a 1 quart V-blender for 10±1 minutes (see Table 1 for weights of individual components of compressible blends of ODTs, 1.5 and 3 mg). A second preblend (preblend 2) is prepared: 10 L granulation bowl of a high shear granulator, PMA 1 is charged with spray-dried mannitol (PARTECK® M200), preblend 1, remaining half of SMCC, crospovidone and sucralose powder. Blending is performed for 10±1 minutes at an impeller speed of 300±50 rpm and a chopper speed of 1500±50 rpm to produce preblend 2. One half of rapidly dispersing microgranules, sodium stearyl fumarate, preblend 2 and the remaining half of rapidly dispersing microgranules are blended in a 8 qt V shell blender and sampled for blend uniformity at 30 and 40 minutes. The final blend is sampled for bulk/tapped density, particle size distribution (PSD), flowability and moisture testing.

TABLE 1

Compositions of compressible blends of Fluticasone ODT's, 1.5 and 3 mg

| | Fluticasone ODTs ODT Batch # | | | | | | |
|---|---|---|---|---|---|---|---|
| | 1.5 mg batch 1 | | 1.5 mg batch 2 | 1.5 mg batch 3 | 1.5 mg batch 4 | 3 mg batch 5 | | 3 mg batch 6 |
| Ingredients (mg) | (%/tablet) | (mg/tablet) | (mg/tablet) | (mg/tablet) | (mg/tablet) | (%/tablet) | (mg/tablet) | (mg/tablet) |
| Micronized Fluticasone Propionate USP | 0.50 | 1.50 | 1.50 | 1.50 | 1.50 | 1.0 | 3.00 | 3.00 |
| Colloidal Silicon Dioxide NF | 0.30 | 0.90 | 0.90 | 0.90 | 0.90 | 0.30 | 0.90 | 0.90 |
| Colloidal Microcrystalline Cellulose NF | 10.00 | 30.00 | 30.00 | 30.00 | 30.00 | 10.00 | 30.00 | 30.00 |
| Crospovidone NF | 7.50 | 22.50 | 22.50 | 22.50 | 22.50 | 7.50 | 22.50 | 22.50 |
| Sucralose NF | 0.40 | 1.20 | 1.20 | 1.20 | 1.20 | 0.40 | 1.20 | 1.20 |

TABLE 1-continued

Compositions of compressible blends of Fluticasone ODT's, 1.5 and 3 mg

|  | Fluticasone ODTs ODT Batch # | | | | | | |
|---|---|---|---|---|---|---|---|
|  | 1.5 mg batch 1 | | 1.5 mg batch 2 | 1.5 mg batch 3 | 1.5 mg batch 4 | 3 mg batch 5 | | 3 mg batch 6 |
| Ingredients (mg) | (%/tablet) | (mg/tablet) | (mg/tablet) | (mg/tablet) | (mg/tablet) | (%/tablet) | (mg/tablet) | (mg/tablet) |
| Spray-dried Mannitol USP | 30.30 | 90.90 | 90.90 | 90.90 | 89.40 | 29.80 | 89.40 | 87.90 |
| Rapidly Dispersing Granules | 50.00 | 150.00 | 150.0 | 150.0 | 150.0 | 50.00 | 150.0 | 150.0 |
| Sodium Stearyl Fumarate NF | 1.00 | 3.00 | 3.00 | 3.00 | 4.50 | 1.00 | 3.00 | 4.50 |
| Total | 100.00 | 300.0 | 300.0 | 300.0 | 300.0 | 100.00 | 300.0 | 300.0 |

Example 3

Blends Preparation by Repeated Blending and Milling for 1.5 and 3 mg Fluticasone ODT; Batch 2, 3 5

A preblend 1 (see Table 1 for weights of individual components of compressible blends of ODTs, 1.5 and 3 mg) is prepared by charging a 2 quart V-blender sequentially with half of SMCC, micronized fluticasone propionate, colloidal silicon dioxide and the remaining half of SMCC and blending for 10±1 minutes. The preblend 1 is passed through a QUADRO Comil fitted with a 024R screen (30 mesh opening) at approximately 2400±100 rpm. Preblend 2 is prepared: half of spray-dried mannitol, milled preblend 1, crospovidone, and sucralose powder are blended in a 4 quart V-blender for 10±1 minutes and milled through the 024R screen. The Comil is rinsed by passing the remaining half of spray-dried mannitol through a 024R screen. Half of rapidly dispersing microgranules, sodium stearyl fumarate, milled preblend 1, rinsed mannitol and the remaining half of rapidly dispersing granules are blended and sampled for blend uniformity at 30 and 40 minutes. The final blends are sampled for testing of bulk/tapped density, particle size distribution (PSD), flowability, and moisture content.

Example 4

Blend Uniformity Results of Blends of Examples 2 and 3

Test results for the compressible blends of Examples 2 and 3 are presented in Table 2. The compression blends, ODT 1.5 mg (batch 1) and ODT 1.5 mg (batch 2), which have been processed using two different combinations of equipment—V-blender-high shear granulator and V-blender-comminuting mill-show similar blend physical (powder) properties such as bulk and tapped densities, particle size distributions, flow properties, and blend uniformity values, excepting that the 30-minute blended batch shows a slightly higher % RSD.

TABLE 2

Physical/Blend uniformity test results for Fluticasone ODT, 1.5 and 3 mg Compressible Blends

| Test | Parameters | | 1.5 mg batch 1 | 1.5 mg batch 2 | 1.5 mg batch 3 | 3 mg batch 5 | 1.5 mg batch 4 | 3 mg batch 6 |
|---|---|---|---|---|---|---|---|---|
| Bulk/Tap Density | Bulk Density | | 0.57 | 0.57 | 0.57 | 0.57 | 0.57 | 0.58 |
| USP <616> Method I | Tapped Density | | 0.71 | 0.71 | 0.72 | 0.70 | 0.78 | 0.77 |
|  | Sieve # | Particle Size (μm) | % Retained | % Retained | % Retained | % Retained | % Retained | % Retained |
| Particle Size | 20 | 840 | 0.62 | 0.39 | 0.36 | 0.61 | 0.6 | 0.4 |
| Analysis | 40 | 425 | 16.08 | 14.05 | 17.32 | 18.08 | 18.9 | 20.2 |
|  | 60 | 250 | 13.37 | 12.00 | 14.57 | 14.62 | 13.8 | 14.8 |
|  | 80 | 180 | 9.70 | 10.33 | 10.07 | 10.21 | 10.7 | 12.0 |
|  | 100 | 150 | 6.60 | 5.84 | 7.90 | 8.37 | 6.2 | 5.5 |
|  | 200 | 75 | 22.61 | 24.62 | 19.83 | 21.24 | 20.0 | 20.0 |
|  | Pan | 20 | 31.01 | 32.77 | 29.95 | 26.86 | 29.8 | 27.1 |
| Flow Results | LOD USP <921> 1a Parameters | | 1.0 | 1.0 | 1.0 | 0.9 | 1.0 | 1.1 |
|  | Flow Angle | | 67.9 | 69 | 55.7 | 55.9 | 68.5 | 67.3 |
|  | Flow Index | | 0.83 | 0.84 | 0.68 | 0.68 | 0.84 | 0.82 |
|  | Flow Quality | | Good | Good | Medium | Medium | Good | Good |
| Blend Uniformity | Blending time | | 30 min | 40 min | 30 min | 40 min | 30 min | 40 min | 40 min | 40 min |
|  | Minimum, % | | 94.8 | 94.5 | 93.2 | 93.4 | 95.8 | 101.0 | 94.7 | 97.3 |
|  | Maximum, % | | 105.1 | 100.4 | 98.6 | 99.9 | 102.8 | 104.8 | 99.4 | 101.1 |
|  | Mean, % | | 99.3 | 97.2 | 95.7 | 97.0 | 98.9 | 102.0 | 97.4 | 99.5 |
|  | % RSD | | 3.6 | 2.2 | 2.0 | 2.9 | 2.7 | 1.4 | 1.0 | 1.5 |

TABLE 2-continued

Physical/Blend uniformity test results for Fluticasone ODT, 1.5 and 3 mg Compressible Blends

| Content | Mean | | | 101.5 | 101.1 | 100.6 | 100.7 |
|---|---|---|---|---|---|---|---|
| Uniformity | ±SD | | | 3.7 | 1.5 | 2.0 | 1.0 |
| | AV | | | 8.8 | 3.7 | 4.7 | 2.4 |

TABLE 3

Stratified Blend uniformity results for Fluticasone ODT Compression Blends

| | Label Claim (%) | | | | | | | |
|---|---|---|---|---|---|---|---|---|
| Sampling | 1.5 mg 101 | | 1.5 mg 201 | | 1.5 mg 301 | 3 mg 101 | | 3 mg 201 |
| Location | 30 min | 40 min | 30 min | 40 min | 40 min | 30 min | 40 min | 40 min |
| Top Left | 98.9 | 96.0 | 95.9 | 99.9 | 94.7 | 100.6 | 101.5 | 98.0 |
| Middle Left | 105.1 | 94.5 | 93.2 | 93.4 | 98.2 | 100.0 | 101.6 | 99.9 |
| Bottom Left | 101.2 | 97.8 | 95.5 | 99.0 | 95.5 | 102.8 | 104.8 | 97.3 |
| Top Right | 94.8 | 95.9 | 94.1 | 93.6 | 98.5 | 96.4 | 101.7 | 101.1 |
| Middle Right | 98.3 | 100.4 | 98.6 | 98.2 | 99.4 | 95.8 | 101.0 | 99.5 |
| Bottom Right | 97.4 | 98.7 | 96.8 | 97.6 | 97.8 | 98.0 | 101.6 | 100.9 |
| Maximum | 105.1 | 100.4 | 98.6 | 99.9 | 99.4 | 102.8 | 104.8 | 101.1 |
| Minimum | 94.8 | 94.5 | 93.2 | 93.4 | 94.7 | 95.8 | 101.0 | 97.3 |
| Mean | 99.3 | 97.2 | 95.7 | 97.0 | 97.4 | 98.9 | 102.0 | 99.5 |
| RSD | 3.6% | 2.2% | 2.0% | 2.9% | 1.9% | 2.7% | 1.4% | 1.5% |

Example 5

Compression of ODTs of Examples 2 and 3

The compression blends of Examples 2 and 3 are compressed using a rotary tablet press, Manesty Beta Press equipped with 8 punch die sets of 9.5 mm round, plain, flat-faced radius edge tooling. The average tablet weight is about 300 mg. The main compression force used is maintained at 5-6 KN, with a pre-compression force set at 2±0.2 kN for compression runs (except where noted). During the compression, the tablet press instrumentation by SMI is used to measure press speed and compression force. During tableting, tablets are periodically sampled for visual inspection of 'appearance', in-process measurements of weight, thickness, hardness and friability. Additional tablets are also samples as 'composite samples' for analytical testing. Details of compression parameters and tablet properties are shown in Table 4. Tablets appears as round tablets they are also tested for assay, potency, content uniformity, dissolution (greater than 90% release after 45 minutes for all batches); they have friability not more than 0.4%, hardness of about 4 kP, disintegration time less than 30 sec.

Example 6

Confirmatory Compression Blend and ODT Batches (ODT 1.5 mg: Batch 3, 3 mg: Batch 5)

Blend batches preparation by a twice repeated blending and milling process (repeated process of blending in the V-shell blender in conjunction with the milling using the Comil) for 1.5 and 3.0 mg fluticasone ODTs compression blends (see Table 1 for compositions, and Tables 2 and 3 for Physical/Blend uniformity test results and Stratified Blend uniformity results, respectively). Although bulk and tapped density values, particle size distributions blend uniformity values for the confirmatory compression blends are similar to those of the corresponding attributes of the ODT compression blend batch, ODT 1.5 mg (batch 2), the estimated flow properties of both ODT 1.5 mg (batch 3) and ODT 3 mg (batch 5) are not very good. Both compression blend batches are compressed using the same Beta Press equipped with the same set of tooling, and under comparable compression parameters. During compression of both compression blends, some picking and/or sticking to the punches is observed. Details of compression parameters and tablet properties are shown in Table 4.

Example 7

Blends Preparation by Repeated Blending and Milling for 1.5 and 3 mg Fluticasone ODT, Lubricant at 1.5% by Weight, Batches 4 and 6

Fluticasone compression blend batches are prepared by first preparing preblend 1 and preblend 2 as disclosed in Example 3, then blending the components of the final blend without incorporating the lubricant for 35 minutes and further blending for 5 minutes following the addition of the lubricant (sodium stearyl fumarate at 1.5% by weight). The final blends are sampled for testing of bulk and tapped density, particle size distribution (PSD), flowability, moisture content, blend uniformity, and stratified blend uniformity of both batches. Results are reported in Tables 2 and 3.

Example 8

Compression of ODTs of Example 7

Both batches are compressed using the same rotary tablet press, same set of tooling and under similar compression conditions as disclosed above.

TABLE 4

Compaction process conditions chemical/physical test results for Fluticasone ODTs

| Compression parameters | 1.5 mg tablet | | | | 3 mg tablet | |
|---|---|---|---|---|---|---|
| | 1.5 mg batch 1 | 1.5 mg batch 2 | 1.5 mg batch 3 | 1.5 mg batch 4 | 3. mg batch 5 | 3 mg batch 6 |
| Compression force (kN) | 5.1-5.5 | 5.1-6.0 | 5.3-5.8 | 5.5-6.0 | 5.1 | 4.7-6.0 |
| Precompression force (kN) | 2.1-2.2 | 2.2 | 2.0-2.2 | 0 | 2.0 | 0 |
| Results | | | | | | |
| Average weight (mg) | 304.3 ± 3.2 | 305.4 ± 3.4 | 303.8 ± 0.7 | 304.7 ± 3.3 | 307 ± 2.1 | 301.8 ± 2.1 |
| Hardness min-max (kp) | 3.23-4.01 | 3.0-3.9 | 2.67-4.12 | 3.8-3.6 | 3.00-3.85 | 3.0-4.2 |
| Thickness min-max (mm) | 4.059-4.149 | 4.02-4.23 | 4.09-4.21 | 4.13-4.19 | 4.28-4.33 | 3.99-4.15 |
| Friability (%) | 0.29 | 0.24 | 0.63 | 0.64 | 0.52 | 0.27 |
| Disintegration - Start (sec) | 12 | 13 | 12 | 12 | 10 | 14 |
| Disintegration - End (sec) | 14 | 14 | 12 | 24 | 16 | 15 |
| Assay % label claim | n.p. | 100.0 | n.p. | 99.2 | 103.8 | 101.6 |
| Related Substances (%) | n.p. | n.p. | n.p. | n.p. | n.p. | n.p. |
| Unknown | n.p. | n.p. | n.p. | <0.10 | <0.10 | <0.10 |
| Unknown | n.p. | 0.11 | n.p. | n.p. | n.p. | n.p. |
| Total | n.p. | 0.11 | n.p. | <0.10 | <0.10 | <0.10 |
| Dissolution (% at x minutes) | | | | | | |
| 10 | 63 | 52 | 69 | 67 | 54 | 54 |
| 20 | 79 | 81 | 86 | 83 | 73 | 73 |
| 30 | 87 | 91 | 93 | 89 | 84 | 82 |
| 45 | 92 | 95 | 96 | 93 | 91 | 88 |
| 60 | 95 | 96 | 98 | 94 | 94 | 90 |

N.P. --> not performed

Example 9

Stability Testing

Fluticasone ODT batches 2 (1.5 mg) and 5 (3 mg) are packaged in 30 cc (30 tablets per bottle) HDPE bottles, with rayon coil and 0.5 g pouch dessicant (Sorb-it ½ g packet) included. All ODTs are stable at accelerated conditions (40° C./75%·RH) for a period of 6 months, as well as at long-term stability conditions (25° C./60% RH) for a period of 9 months as shown in Tables 5 and 6. The physical properties, such as appearance, hardness, friability, and disintegration time at all stability conditions are also comparable to the initial values of Fluticasone ODTs, 1.5 and 3 mg.

TABLE 5

Stability data for Fluticasone ODT batch 2 (1.5 mg)

| | Batch 2, 1.5 mg | | | | | |
|---|---|---|---|---|---|---|
| Test/Method | Time = Initial | | Time = 6 months 40° C./75% RH | | Time = 9 months 25° C./60% RH | |
| Physical Appearance/Visual | White round tablets | | White round tablets | | White round tablets | |
| Moisture | 1.0% | | 1.9% | | 1.8% | |
| Disintegration | 16 sec | | 25 sec | | 18 sec | |
| Friability | 0.3% | | 0.6% | | 0.1% | |
| Hardness (kP) | Min: 2.2 Max: 3.6 Mean: 3.0 | | Min: 1.4 Max: 3.3 Mean: 2.5 | | Min: 2.7 Max: 4.3 Mean: 3.4 | |
| Potency (%) | 1: 100.0 2: 100.0 Mean. 100.0 | | 1: 100.0 2: 100.2 Mean: 100.1 | | 1: 99.5 2: 98.3 Mean: 98.9 | |
| Related Substances, | RRT | % RS | RRT | % RS | RRT | % RS |
| Unknown | — | — | 0.89 | 0.14 | 1.66 | 0.10 |
| Unknown | 0.75 | 0.11 | 0.90 | 0.13 | — | — |
| Total (%) | | 0.11 | | 0.27 | | 0.10 |
| Dissolution | | | | | | |

| Minutes | 10 | 20 | 30 | 45 | 60 | 10 | 20 | 30 | 45 | 60 | 10 | 20 | 30 | 45 | 60 |
|---|---|---|---|---|---|---|---|---|---|---|---|---|---|---|---|
| Minimum (%) | 61 | 82 | 90 | 93 | 95 | 66 | 84 | 92 | 96 | 97 | 66 | 83 | 90 | 93 | 94 |
| Maximum (%) | 67 | 86 | 94 | 97 | 99 | 68 | 86 | 93 | 97 | 99 | 69 | 85 | 91 | 95 | 96 |

TABLE 5-continued

Stability data for Fluticasone ODT batch 2 (1.5 mg)

| Mean (%) | 64 | 85 | 92 | 95 | 97 | 67 | 85 | 92 | 96 | 98 | 67 | 84 | 91 | 94 | 95 |
|---|---|---|---|---|---|---|---|---|---|---|---|---|---|---|---|
| % RSD | 3.3 | 2.1 | 1.7 | 1.7 | 1.7 | 1.0 | 0.7 | 0.7 | 0.8 | 0.8 | 1.8 | 0.9 | 0.8 | 0.8 | 0.8 |

TABLE 6

Stability data for Fluticasone ODT batch 5 (3 mg)

Batch 5, 3 mg

| Test/Method | Time = Initial | Time = 6 months 40° C./75% RH | Time = 9 months 25° C./60% RH |
|---|---|---|---|
| Physical Appearance/Visual | White round tablets | White round tablets | White round tablets |
| Moisture Content | 0.9% | 1.3% | 1.8% |
| Disintegration Time | 17 sec | 17 sec | 15 sec |
| Friability | 1.2% | 1.6% | 1.1% |
| Hardness (kP) | Min: 1.9 Max: 3.5 Mean: 2.6 | Min: 1.3 Max: 3.7 Mean: 2.5 | Min: 1.7 Max: 3.0 Mean: 2.4 |
| Potency (%) | 1: 103.6 2: 103.9 Mean. 103.8 | 1: 99.8 2: 97.4 Mean. 98.6 | 1: 100.7 2: 100.1 Mean. 100.4 |

| Related Substances, | RRT | % RS | RRT | % RS | RRT | % RS |
|---|---|---|---|---|---|---|
| Unknown | 0.89 | <0.1 | 0.89 | 0.14 | 1.66 | 0.13 |
| Unknown | — | — | 0.90 | 0.13 | — | — |
| Total (%) | | <0.1 | | 0.27 | | 0.10 |

Dissolution

| Minutes | 10 | 20 | 30 | 45 | 60 | 10 | 20 | 30 | 45 | 60 | 10 | 20 | 30 | 45 | 60 |
|---|---|---|---|---|---|---|---|---|---|---|---|---|---|---|---|
| Minimum (%) | 57 | 78 | 87 | 92 | 94 | 47 | 64 | 72 | 78 | 80 | 56 | 76 | 85 | 91 | 93 |
| Maximum (%) | 61 | 81 | 90 | 95 | 97 | 56 | 76 | 89 | 97 | 101 | 59 | 78 | 89 | 96 | 99 |
| Mean (%) | 59 | 79 | 88 | 94 | 96 | 53 | 73 | 84 | 91 | 94 | 58 | 77 | 86 | 93 | 95 |
| % RSD | 3.1 | 1.7 | 1.4 | 1.4 | 1.3 | 6.1 | 6.4 | 7.0 | 7.4 | 7.6 | 1.5 | 1.2 | 1.7 | 2.0 | 2.2 |

Example 10

Preparation of Clinical Trial Materials, Batches C1, C2

Clinical trial batches (Fluticasone propionate ODTs, 1.5 and 3 mg with 1.5% by weight of sodium stearyl fumarate) are prepared by a repeated blending—milling-blending process followed by compression as disclosed in Examples 7 and 8. The in-process testing results and the analytical results of the clinical batches are presented in Table 7 and Table 8, respectively. The compression blend batches show physical (powder) properties similar to that of the feasibility batches, except that the clinical batches have more finer particles passing through 100 mesh sieve (67-76% particles are <150 μm in size) as compared to 47-57%) finer particles in the feasibility batches. However, this has not affected the tableting properties of the clinical batches significantly; in batch C-2 (3 mg) a slightly higher % RSD In content uniformity and excellent blend uniformity results are observed.

TABLE 7

Physical/Blend uniformity test results for Clinical Trial Batches 1.5 and 3 mg

| | | 1.5 mg Blend | | 3 mg Blend | |
|---|---|---|---|---|---|
| Test/Method | Test Parameter | 1.5001 | 1.5002 | 3.0001 | 3.0002 |
| Bulk/Tap Density USP <616> Method 1 | Bulk Density (g/cc) | 0.56 | 0.56 | 0.56 | 0.56 |
| | Tapped Density (g/cc) | 0.75 | 0.75 | 0.75 | 0.74 |
| | Hausner Ratio | 1.34 | 1.34 | 1.34 | 1.32 |
| | Carr's Index | 25.14 | 25.41 | 25.56 | 24.44 |

TABLE 7-continued

Physical/Blend uniformity test results for Clinical Trial Batches 1.5 and 3 mg

| | Size/ | Particle Size (µm) | % Retained | % Retained | % Retained | % Retained |
|---|---|---|---|---|---|---|
| Particle Size | 20 | 840 | 0.50 | 0.80 | 0.20 | 0.70 |
| Analysis | 40 | 425 | 2.90 | 3.30 | 7.30 | 3.40 |
| | 60 | 250 | 6.00 | 10.60 | 5.10 | 9.90 |
| | 80 | 180 | 8.90 | 11.40 | 9.30 | 10.80 |
| | 100 | 150 | 5.50 | 6.00 | 6.10 | 5.70 |
| | 200 | 75 | 23.20 | 23.40 | 24.40 | 21.40 |
| | Pan | <75 | 53.00 | 44.50 | 52.60 | 48.10 |
| | LOD (USP <921>1a | | 1.3 | 1.2 | 1.6 | 1.2 |
| Blend | Minimum (%) | | 97.4 | 94.0 | 96.4 | 94.1 |
| Uniformity | Maximum (%) | | 98.1 | 97.0 | 99.1 | 96.2 |
| | Mean (%) | | 97.9 | 96.1 | 98.1 | 95.8 |
| | % RSD | | 0.3 | 1.2 | 0.9 | 0.9 |

TABLE 8

Physical/Blend uniformity test results for Clinical Trial Batches of Fluticasone ODTs, 1.5 and 3 mg

| Parameter | ODT 1.5 mg C1 | ODT 1.5 mg C2 | ODT 3 mg C1 | ODT 3 mg C2 |
|---|---|---|---|---|
| Physical Appearance/Visual | White round tablets | White round tablets | White round tablets | White round tablets |
| Moisture Content | 1.9% | 1.2% | 1.8% | 1.3% |
| Disintegration Time | 15 sec | 18 sec | 16 sec | 19 sec |
| Friability | 0.1% | 0.0% | 0.4% | 0.3% |
| Hardness, kP | Min: 3.1 | Minimum: 3.9 | Minimum: 2.8 | Minimum: 3.5 |
| | Max: 5.1 | Maximum: 5.4 | Maximum: 4.3 | Maximum: 4.9 |
| | Mean: 3.9 | Mean: 4.6 | Mean: 3.4 | Mean: 4.3 |
| Potency (%) | 1: 98.3 | 1: 95.4 | 1: 98.3 | 1: 98.1 |
| | 2: 99.2 | 2: 96.1 | 2: 99.6 | 2: 97.9 |
| | Mean: 98.8 | Mean: 95.8 | Mean: 99.0 | Mean: 98.0 |
| Related Substance (%) | % RS at RRT | % RS at RRT | % RS at RRT | % RS at RRT |
| Individual Impurity (NMT 0.5%) | <0.1% at 0.89 | <0.10 | <0.10 | <0.10 |
| Total (NMT 1.5%) | <0.1% at 0.90 | <0.10 | <0.10 | <0.10 |
| Content Uniformity of Dosage units - Minimum (%) | 97.0 | 93.2 | 98.3 | 96.1 |
| — Maximum | 99.3 | 97.9 | 100.4 | 98.5 |
| — Mean | 98.1 | 96.3 | 99.2 | 97.5 |
| — % RSD | 2.3 | 6.1 | 1.7 | 3.7 |
| % Mean Dissolved/60 min | 96% | 95% | 94% | 93% |

Example 11

Stability Data for Clinical Trial Batches, Fluticasone ODTs, 1.5 and 3 mg

Fluticasone ODT batches, 1.5 mg and 3 mg are packaged in 30 c't (30 tablets per bottle) HDPE bottles, with rayon coil and 0.5 g pouch dessicant (Sorb-it ½ g packet) included. All ODTs are stable at accelerated conditions (40° C./75% RH) for a period of 9 months, as well as at long-term stability conditions (25° C./60% RH) for a period of 24 months as shown in Table 9. The physical properties, such as appearance, hardness, friability, and disintegration time at all stability conditions are also comparable to the initial values of Fluticasone ODTs, 1.5 and 3 mg.

TABLE 9

Stability data for Clinical Trial Batches Fluticasone ODTs, 1.5 and 3 mg

| ODT Batch # | ODTs, 1.5 mg | | ODTs, 3 mg | |
|---|---|---|---|---|
| Parameter | Time: Initial | Time: 24 months at 25° C./60% RH | Time: Initial | Time: 24 months at 25° C./60% RH |
| Physical Appearance/Visual | White round tablets | White round tablets | White round tablets | White round tablets |
| Moisture Content | 2.2% | 2.1% | 2.4% | 2.0% |
| Disintegration Time | 0-5 sec | 0-5 sec | 0-5 sec | 0-5 sec |
| Friability | 0.03% | 0.12% | 0.02% | 0.50% |
| Hardness, kP | Min: 3.6 | Min: 3.8 | Min: 4.0 | Min: 3.3 |
| | Max: 6.1 | Max: 5.9 | Max: 5.9 | Max: 6.2 |
| | Mean: 4.8 | Mean: 5.0 | Mean: 4.7 | Mean: 4.8 |

TABLE 9-continued

Stability data for Clinical Trial Batches Fluticasone ODTs, 1.5 and 3 mg

| ODT Batch # | ODTs, 1.5 mg | | ODTs, 3 mg | |
|---|---|---|---|---|
| Potency (%) | 1: 100.8 | 1: 99.7 | 1: 100.3 | 1: 100.0 |
|  | 2: 100.3 | 2: 99.8 | 2: 101.3 | 2: 100.0 |
|  | Mean: 100.6 | Mean: 99.7 | Mean: 100.8 | Mean: 100.0 |
| Related Substances | % RS at RRT | % RS at RRT | % RS at RRT | % RS at RRT |
| Unknown | <0.1% at 0.89 | — | <0.1% at 0.89 | — |
| Unknown | <0.1% at 0.90 | — | <0.1% at 0.90 | — |
| Total | <0.1 | <QL | <0.1 | <QL |
| % Mean Dissolved/ 60 min | 96% | 95% | 94% | 93% |

Example 12

Clinical Tests

A proof of concept study is conducted for clinical batches ODT-FT 1.5 mg and 3 mg dose strengths in patients with a diagnosis of EoE aged 12 years to 55 years.

The doses utilized are 1.5 mg administered twice daily and 3.0 mg administered once daily. The study also included a placebo arm. Each arm enrolls 8 subjects. Findings of efficacy analyses demonstrate a positive signal for efficacy with the greatest response seen histologically in the decrease of peak eosinophil count per high power field (a hallmark of the disease and indicator of treatment response). Both 1.5 mg and 3 mg treatment groups are clearly more efficacious than placebo histologically. The percent of subjects with at least 30% decrease in the overall EoE symptom severity, as measured by patient questionnaire, also shows numerical superiority of the two FT-ODTs over placebo. Endoscopic improvements are also seen with changes in furrowing and vascularity showing the greatest differentiation of FT-ODTs from placebo, indicating a positive anti-inflammatory effect of the formulations.

Overall, the FT-ODTs of the invention demonstrate improvements in histology, overall symptoms and overall endoscopic activity.

Example 13

Preparation of Blends for 0.75, 4.5 and 6 mg Fluticasone ODTs—Batches 7 to 9

Fluticasone compression blend batches at a drug load of 0.25% by weight are prepared by first preparing preblend 1 and pre blend 2 as disclosed in Example 3. A preblend 1 (see Table 10 for weights of individual components of compression blends of ODTs, 0.75 mg, 4.5 mg and 6 mg) is prepared by charging a 2 quart V-blender sequentially with half of SMCC, micronized fluticasone propionate, colloidal silicon dioxide and the remaining half of SMCC and blending at 25 rpm for 10±1 minutes. The preblend 1 is passed through a QUADRO Comil fitted with a 024R screen (30 mesh opening) at approximately 2400±100 rpm. Preblend 2 is prepared: half of spray-dried mannitol, milled preblend 1, crospovidone, and sucralose powder are blended in a 32 quart V-blender at 25 rpm for 10±1 minutes and milled through the 024R screen. The Comil is rinsed by passing the remaining half of spray dried mannitol through a 024R screen. Half of rapidly dispersing microgranules, milled preblend 1, rinsed mannitol and the remaining half of rapidly dispersing granules are blended in a 32 quarts V-blender at 25 rpm, without incorporating the lubricant, for 35 minutes and further blended for 5 minutes following the addition of the lubricant (sodium stearyl fumarate at 1.5% by weight).

Example 14

Preparation of Blends for 1.5 mg Fluticasone ODTs at Batch Size: 30 kgs; batch 10

The manufacturing process for the fluticasone compression blend batch at a lower drug load of 0.5% by weight is scaled up to a semi-industrial scale of 30 kgs. The process essentially consists of first preparing preblend 1 and preblend 2 as disclosed in Example 3. A preblend 1 (see Table 10 for weights of individual components of compressible blends of ODTs, 1.5 mg) is prepared by charging a 32 quart V-blender sequentially with half of SMCC, micronized fluticasone propionate, colloidal silicon dioxide and the remaining half of SMCC and blending at 25 rpm for 10±1 minutes. The preblend 1 is passed through a QUADRO Comil fitted with a 024R screen (30 mesh opening) at approximately 2400±100 rpm. Preblend 2 is prepared: half of spray-dried mannitol, milled preblend 1, crospovidone, and sucralose powder are blended in a Galley blender with 113 L tote at 12 rpm for 20±1 minutes and milled through the 024R screen. The Comil is rinsed by passing the remaining half of spray-dried mannitol through a 024R screen. Half of rapidly dispersing microgranules, milled preblend 1, rinsed mannitol and the remaining half of rapidly dispersing granules are blended at 12 rpm for up to 40 minutes.

The final blends in Example 13 and 14 are sampled and subjected to in-process testing as per United States Pharmacopeia requirements and analytical testing of bulk and tapped density, particle size distribution (PSD), flowability, blend uniformity and moisture content. This is the first time, a direct compression ODT blend batch at a drug load of 0.25% by weight is manufactured using the procedure established for the blend at a drug load of 0.5% by weight. No technical issues have been encountered during the manufacture. The results reported in Table 11 show acceptable physical characteristics. Although the blend uniformity data indicate a uniform distribution of the active, a low potency is evident in Batch 7 with the lowest drug load, probably due to a loss of the active during blending/milling. During the semi-industrial scale compression blending process prior to incorporating the lubricant, the blends sampled at 20, 30 and 40 minutes show acceptable blend uniformity values as shown below.

| | Sampling Time | 20 min | 30 min | 40 min |
|---|---|---|---|---|
| Blend Uniformity (% Label Claim) | Mean (%) | 101.4 | 99.1 | 98.3 |
| | Minimum (%) | 99.3 | 97.2 | 95.9 |
| | Maximum (%) | 104.3 | 100.6 | 100.1 |
| | RSD (%) | 1.4 | 1.4 | 1.3 |

Example 15

Compression of ODTs of Example 13 and 14

Batches of ODTs, 0.75 mg, 4.5 mg and 6 mg are compressed using the same rotary tablet press (Beta Press) equipped with the same force feeder and same set of tooling (B-size tooling, 9.5 mm round flat faced radius edge) and under similar compression conditions as disclosed previously for ODTs, 1.5 mg or 3 mg. The compressed tablets of 0.75 mg, 4.5 mg and 6 mg meet the specifications for tablet weight, disintegration time, friability, hardness and thickness. The physical properties of the tablets are similar and comparable to the other dose strengths. The potency and content uniformity results for the 0.75 mg ODTs indicate a low potency confirming the low blend uniformity results reported above.

ODTs, 1.5 mg are compressed using the industrial tablet press, Korsch XL 400 equipped with D tooling, 9.5 mm round, flat faced radius edge, operated at 1015 tablets per minutes. The compressed tablets are observed to meet all specifications for tablet weight, disintegration time, friability, hardness and tablet thickness. The physical properties of the tablets are similar and comparable to the same dose strength or other dose strengths produced at small scale. The potency and content uniformity results confirm the blend uniformity results, resulting ODTs meeting all product specifications. The results of the scale up batch have shown that the current small-scale process at a drug load of 0.5% by weight or higher, is scalable. The comparable/similar results obtained between dose strengths and consistency in results between batch sizes at least at a drug load of 0.5% by weight or higher, indicate a robust, suitable direct compression manufacturing process for ODT dose strengths ranging from 1.5 mg to 6 mg or at a drug load of from 0.5%, to 2% by weight. This low-end drug load has been possible in the past only by spray granulation, by spraying the drug solution while granulating tablet components excepting the lubricant.

TABLE 10

Compositions of compression blends of Fluticasone ODTs, 0.75 mg (Batch 7), 4.5 mg (Batch 8), 6 mg (Batch 9) and 1.5 mg (Batch 10)

| | Fluticasone ODTs ODT Batch # | | | | |
|---|---|---|---|---|---|
| | 0.75 mg batch 7 | | 4.5 mg batch 8 | 6.0 mg batch 9 | 1.5 mg batch 10 |
| Ingredients (mg) | (%/tablet) | (mg/tablet) | (mg/tablet) | (mg/tablet) | (mg/tablet) |
| Micronized Fluticasone Propionate USP | 0.25 | 0.75 | 4.50 | 6.00 | 1.50 |
| Colloidal Silicon Dioxide NF | 0.30 | 0.90 | 0.90 | 0.90 | 0.90 |
| Silicified Microcrystalline Cellulose NF | 10.00 | 30.0 | 30.00 | 30.00 | 30.00 |
| Crospovidone NF | 7.50 | 22.50 | 22.50 | 22.50 | 22.50 |
| Sucralose NF | 0.40 | 1.20 | 1.20 | 1.20 | 1.20 |
| Spray-dried Mannitol USP | 30.05 | 90.15 | 86.40 | 84.90 | 89.40 |
| Rapidly Dispersing Granules | 50.00 | 150.00 | 150.00 | 150.0 | 150.0 |
| Sodium Stearyl Fumarate NF | 1.50 | 4.50 | 4.50 | 4.50 | 4.50 |
| Total | 100.00 | 300.00 | 300.00 | 300.00 | 300.00 |

TABLE 11

Physical/Blend uniformity test results for Fluticasone ODT, 0.75 mg, 4.5 mg and 6 mg Compression Blends

| | | Blend Batch # | | |
|---|---|---|---|---|
| Test | Parameters | 0.75 mg batch 7 | 4.5 mg batch 8 | 6.0 mg batch 9 |
| Bulk/Tap Density USP <616> Method I | Bulk Density | 0.56 | 0.55 | 0.55 |
| | Tapped Density | 0.75 | 0.73 | 0.75 |
| | Hausner Ratio | 1.33 | 1.33 | 1.33 |
| | Sieve # | Particle Size (μm) | % Retained | % Retained | % Retained |
| Particle Size Analysis | 20 | 840 | 0.6 | 0.6 | 0.6 |
| | 40 | 425 | 10.0 | 9.8 | 7.6 |

TABLE 11-continued

Physical/Blend uniformity test results for Fluticasone
ODT, 0.75 mg, 4.5 mg and 6 mg Compression Blends

| | | | Blend Batch # | | |
|---|---|---|---|---|---|
| Test | Parameters | | 0.75 mg batch 7 | 4.5 mg batch 8 | 6.0 mg batch 9 |
| | 60 | 250 | 16.9 | 16.7 | 15.1 |
| | 80 | 180 | 20.2 | 19.2 | 18.5 |
| | 100 | 150 | 9.3 | 9.3 | 9.4 |
| | 200 | 75 | 25.2 | 26.9 | 28.4 |
| | Pan | 20 | 17.8 | 17.5 | 20.5 |
| | LOD USP <921> (KF) | | 1.4 | 1.8 | 1.5 |
| Flow Results | Flow Angle | | 82.6 | 83.9 | 83.2 |
| | Flow Index | | 1.01 | 1.02 | 1.01 |
| | Flow Quality | | Very Good | Very Good | Medium |
| Blend Uniformity | Blending Time | | Blend (40 min) After Lubrication | | |
| | Mean, % | | 91.3 | 97.1 | 98.7 |
| | Minimum, % | | 88.5 | 94.7 | 94.7 |
| | Maximum, % | | 94.1 | 98.7 | 100.4 |
| | % RSD | | 2.2 | 1.3 | 2.1 |

TABLE 12

Compaction process conditions and chemical/physical test results for Fluticasone ODTs

| | ODTs | | | |
|---|---|---|---|---|
| Compression parameters | 0.75 mg batch 7 | 4.5 mg batch 8 | 6.0 mg batch 9 | 1.5 mg batch 10 |
| Compression force (kN) | 5.3-5.6 | 5.0-5.2 | 5.2-5.3 | 4.8-5.1 |
| Precompression force (kN) | 2.0 | 1.5-1.7 | 1.5 | 1.3-1.4 |
| Average weight, mg (% RSD)* | 302.3 (0.56) | 301.9 (0.84) | 300.6 (0.54) | 301.2 (0.76) |
| | 297.3 (0.58) | 301.7 (0.94) | 303.6 (0.42) | 302.2 (0.40) |
| | 296.4 (0.40) | 303.2 (0.77) | 299.6 (0.76) | 302.1 (0.33) |
| Hardness min-max (kp)* | 3.70 (2.4-5.9) | 3.35 (3.0-3.9) | 4.34 (3.8-4.8) | 4.45 (4.9-5.8) |
| | 3.57 (2.4-5.9) | 3.72 (2.8-4.4) | 3.13 (2.3-3.4) | 4.92 (3.8-5.5) |
| | 2.95 (2.8-3.2) | 3.75 (3.1-4.6) | 3.14 (2.1-4.0) | 4.91 (4.6-5.4) |
| Thickness min-max (mm) | 4.15-4.41 | 4.01-4.12 | 4.01-4.19 | 4.01-4.04 |
| Friability (%) Start/Middle/End | 0.2/0.2/0.3 | 0.5/0.2/0.3 | 0.5/0.5//0.3 | 0.0/0.1/0.0 |
| Disintegration - Start (sec) | 10 | 15 | 15 | 12 |
| Disintegration - End (sec) | 10 | 14 | 16 | 14 |
| Assay % label claim | 95.5-95.6 | 98.6 | 99.3-100.1 | 97.2-99.3 |
| Related Substances (%) - RRT | | | | |
| Unknown 0.79 | | ND | ND | 0.18 |
| Unknown 0.89/0.90 | | ND/0.10 | ND/ND | <0.10/0.11 |
| Unknown 1.58 /1.84 | | ND/ND | ND/ND | <0.10/<0.10 |
| Total | | 0.10 | <0.10 | 0.29 |
| Time | % Dissolved | | | |
| 10 Min | 58 (1.9) | 46 (2.6) | 46 (3.1) | 64 (2.5) |
| 20 Min | 72 (1.1) | 74 (15.2) | 66 (1.1) | 82 (0.9) |
| 30 Min | 79 (0.9) | 85 (8.8) | 77 (1.2) | 90 (1.2) |
| 45 Min | 84 (0.8) | 89 (2.8) | 86 (1.5) | 93 (1.0) |
| 60 Min | 86 (0.6) | 92 (1.0) | 91 (1.4) | 95 (1.0) |

*--> Tested at Start, Middle and End of compression;
ND --> not detected

Stability of Fluticasone ODTs batch 7 (0.75 mg), batch 8 (4.5) and batch 9 (6 mg) is testes; these batches are packaged in 30 cc (30 tablets per bottle) HDPE bottles, with rayon coil and 0.5 g silica pouch dessicant (Sorb-it ½ g packet) included. All ODTs are stable at accelerated conditions (40° C./75% RH) for a period of 6 months, as well as at long-term stability conditions (25° C./60% RH) for a period of 9 months; all values measured at given time points (T=0, 1 month, 2 months, 3 months, 6 months, 9 months) are within the acceptance criteria (disintegration: NMT 30 sec, assay: NLT 90.0% and NMT 110.0%, each impurity: NMT 0.5%, total impurity: NMT 1.5%). The physical properties, such as appearance, hardness, friability, and disintegration time at all stability conditions are also comparable to the initial values of the corresponding Fluticasone ODTs.

While the invention has been described in connection with the specific embodiments herein, it will be understood that it is capable of further modifications and this application is intended to cover any variations, uses, or adaptations of the invention following, in general, the principles of the invention and including such departures from the present disclosure as come within known or customary practice within the art to that the invention pertains and as may be applied to the essential features hereinbefore set forth and as follows in the scope of the appended claims.

What is claimed is:

1. An orally disintegrating tablet comprising:
   a. fluticasone or ester thereof, adsorbed onto a pharmaceutically acceptable carrier; and
   b. at least one disintegrant;
   wherein the fluticasone or ester thereof is present in an amount ranging from about 0.5 mg to about 10 mg, and the fluticasone or ester thereof has a mean particle size ranging from about 100 μm to about 100 nm; and
   wherein the orally disintegrating tablet disintegrates within 60 seconds when tested using the USP <701>method for disintegration time;
   wherein the orally disintegrating tablet is prepared by a method comprising the steps of:
   preparing preblend 1 by blending (i) the pharmaceutically acceptable carrier, (ii) fluticasone or ester thereof, and (iii) glidant, under conditions suitable for the fluticasone or ester thereof to be adsorbed onto the pharmaceutically acceptable carrier.

2. The orally disintegrating tablet of claim 1, wherein the pharmaceutically acceptable carrier is selected from the group consisting of microcrystalline cellulose, silicified microcrystalline cellulose, pregelatinized starch, corn starch, colloidal silica, and amorphous magnesium aluminum silicate.

3. The orally disintegrating tablet of claim 2, wherein the pharmaceutically acceptable carrier is silicified microcrystalline cellulose.

4. The orally disintegrating tablet of claim 1, wherein the fluticasone or ester thereof is present in an amount ranging from about 0.5 mg to about 3 mg.

5. The orally disintegrating tablet of claim 1, wherein said fluticasone or ester thereof is fluticasone propionate.

6. The orally disintegrating tablet of claim 5, wherein fluticasone propionate is present in an amount of about 3 mg in the orally disintegrating tablet.

7. The orally disintegrating tablet of claim 5, wherein fluticasone propionate is present in an amount of about 1.5 mg in the orally disintegrating tablet.

8. The orally disintegrating tablet of claim 1, wherein the fluticasone or ester thereof has a mean particle size ranging from about 10 μm to about 100 nm.

9. The orally disintegrating tablet of claim 1, wherein the fluticasone or ester thereof has a mean particle size ranging from about 4 μm to about 100 nm.

10. The orally disintegrating tablet of claim 1, comprising a rapidly dispersing microgranule, wherein a disintegrant is present in the rapidly dispersing microgranule, and the rapidly dispersing microgranule comprises a sugar alcohol, or a saccharide, or a mixture thereof in addition to the at least one disintegrant.

11. The orally disintegrating tablet of claim 10, wherein the sugar alcohol or saccharide and a disintegrant are present in a ratio of sugar alcohol or saccharide to disintegrant of from 90:10 to 99:1.

12. The orally disintegrating tablet of claim 10, wherein the disintegrant is selected from the group consisting of crospovidone, sodium starch glycolate, crosslinked carboxymethyl cellulose, and low-substituted hydroxylpropylcellulose.

13. The orally disintegrating tablet of claim 10, wherein the sugar alcohol or saccharide is selected from the group consisting of sucralose, lactose, sucrose, maltose, mannitol, sorbitol, xylitol, maltitol, and mixtures thereof.

14. The orally disintegrating tablet of claim 10, wherein the rapidly dispersing microgranule has a mean particle size of less than about 300 μm, and the sugar alcohol and/or saccharide has an average particle size of less than about 30 μm.

15. The orally disintegrating tablet of claim 1, wherein the pharmaceutically acceptable carrier is present at an amount of about 10% w/w based on the total weight of the orally disintegrating tablet.

16. The orally disintegrating tablet of claim 1, wherein the total weight of the orally disintegrating tablet is in the range of from about 300 to about 900 mg.

17. The orally disintegrating tablet of claim 1, wherein fluticasone propionate has a mean particle size of about 4 μm or less.

18. The orally disintegrating tablet of claim 1, comprising preparing preblend 2 by blending filler, preblend 1, the at least one disintegrant, and sweetener.

19. The orally disintegrating tablet of claim 18, comprising preparing a final compressible blend, by blending the at least one disintegrant, lubricant, filler, and preblend 2.

20. The orally disintegrating tablet of claim 19, comprising compressing the final compressible blend to form the orally disintegrating tablet.

* * * * *